United States Patent
Froelich et al.

(10) Patent No.: US 11,123,443 B2
(45) Date of Patent: *Sep. 21, 2021

(54) HTT REPRESSORS AND USES THEREOF

(71) Applicant: Sangamo Therapeutics, Inc., Richmond, CA (US)

(72) Inventors: Steven Froelich, Richmond, CA (US); Jeffrey C. Miller, Richmond, CA (US); David Paschon, Richmond, CA (US); Edward J. Rebar, Richmond, CA (US); Bryan Zeitler, Richmond, CA (US); H. Steve Zhang, Richmond, CA (US)

(73) Assignee: Sangamo Therapeutics, Inc., Brisbane, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/550,949

(22) Filed: Aug. 26, 2019

(65) Prior Publication Data
US 2020/0002390 A1    Jan. 2, 2020

Related U.S. Application Data

(63) Continuation of application No. 15/274,357, filed on Sep. 23, 2016, now Pat. No. 10,435,441.

(60) Provisional application No. 62/222,588, filed on Sep. 23, 2015.

(51) Int. Cl.
| | | |
|---|---|---|
| A61K 48/00 | (2006.01) | |
| C07K 14/47 | (2006.01) | |
| C12N 15/864 | (2006.01) | |
| C12N 15/86 | (2006.01) | |
| C12N 5/077 | (2010.01) | |
| C12N 5/10 | (2006.01) | |
| C12N 5/0793 | (2010.01) | |

(52) U.S. Cl.
CPC .......... *A61K 48/0075* (2013.01); *A61K 48/00* (2013.01); *C07K 14/47* (2013.01); *C07K 14/4702* (2013.01); *C07K 14/4703* (2013.01); *C12N 5/0619* (2013.01); *C12N 5/0656* (2013.01); *C12N 5/10* (2013.01); *C12N 15/86* (2013.01); *C12N 15/8645* (2013.01); *C07K 2319/81* (2013.01)

(58) Field of Classification Search
CPC .... A61K 48/0075; A61K 48/00; C12N 15/86; C12N 15/8645; C12N 5/10; C12N 5/0656; C12N 5/0619; C07K 14/4702; C07K 14/4703; C07K 14/47; C07K 2319/81
USPC .............. 514/44 R; 435/320.1, 325; 530/350
See application file for complete search history.

(56) References Cited

U.S. PATENT DOCUMENTS

| | | |
|---|---|---|
| 5,789,538 A | 8/1998 | Rebar et al. |
| 5,925,523 A | 7/1999 | Dove et al. |
| 5,928,638 A | 7/1999 | Uchida et al. |
| 6,007,988 A | 12/1999 | Choo et al. |
| 6,013,453 A | 1/2000 | Choo et al. |
| 6,140,081 A | 10/2000 | Barbas |
| 6,200,759 B1 | 3/2001 | Dove |
| 6,309,634 B1 | 10/2001 | Bankiewicz |
| 6,453,242 B1 | 9/2002 | Eisenberg et al. |
| 6,503,717 B2 | 1/2003 | Case et al. |
| 6,534,261 B1 | 3/2003 | Cox, III |
| 6,599,692 B1 | 7/2003 | Case |
| 6,607,882 B1 | 8/2003 | Cox, III |
| 6,689,558 B2 | 2/2004 | Case |
| 6,746,838 B1 | 6/2004 | Choo |
| 6,824,978 B1 | 11/2004 | Cox, III |
| 6,866,997 B1 | 3/2005 | Choo |
| 6,933,113 B2 | 8/2005 | Case |
| 6,953,575 B2 | 10/2005 | Bankiewicz et al. |
| 6,979,539 B2 | 12/2005 | Cox, III et al. |
| 7,013,219 B2 | 3/2006 | Case et al. |
| 7,067,317 B2 | 6/2006 | Rebar et al. |
| 7,074,596 B2 | 7/2006 | Darzynkiewicz et al. |
| 7,163,824 B2 | 1/2007 | Cox, III |
| 7,182,944 B2 | 2/2007 | Bankiewicz |
| 7,241,573 B2 | 7/2007 | Choo et al. |
| 7,241,574 B2 | 7/2007 | Choo et al. |
| 7,262,054 B2 | 8/2007 | Jamieson et al. |
| 7,837,668 B2 | 11/2010 | Gasmi et al. |
| 7,888,121 B2 | 2/2011 | Urnov |
| 7,914,796 B2 | 3/2011 | Miller et al. |
| 7,951,925 B2 | 5/2011 | Ando et al. |
| 7,972,854 B2 | 7/2011 | Miller et al. |
| 8,034,598 B2 | 10/2011 | Miller |
| 8,092,429 B2 | 1/2012 | Gasmi et al. |
| 8,110,379 B2 | 2/2012 | DeKelver |
| 8,153,773 B2 | 4/2012 | Jemielity et al. |
| 8,309,355 B2 | 11/2012 | Bankiewicz |
| 8,337,458 B2 | 12/2012 | Bankiewicz et al. |

(Continued)

FOREIGN PATENT DOCUMENTS

| | | |
|---|---|---|
| EP | 2441774 A1 | 4/2012 |
| WO | WO 95/19431 A1 | 7/1995 |

(Continued)

OTHER PUBLICATIONS

Garriga-Canut et al. (2012) PNAS, Early Edition, www.pnas.org/cgi/doi/10.1073/pnas.1206506109, pp. 1-10.*

(Continued)

*Primary Examiner* — Anne Marie S Wehbe

(74) *Attorney, Agent, or Firm* — Foley & Lardner LLP

(57) ABSTRACT

Disclosed herein are Htt repressors and methods and compositions for use of these Htt repressors.

9 Claims, 16 Drawing Sheets

Specification includes a Sequence Listing.

(56) References Cited

U.S. PATENT DOCUMENTS

| | | | |
|---|---|---|---|
| 8,409,861 | B2 | 4/2013 | Guschin et al. |
| 8,586,526 | B2 | 11/2013 | Gregory et al. |
| 8,597,912 | B2 | 12/2013 | Collingwood et al. |
| 8,623,618 | B2 | 1/2014 | Doyon et al. |
| 8,703,489 | B2 | 4/2014 | Wang |
| 8,841,260 | B2 | 9/2014 | Miller et al. |
| 8,945,868 | B2 | 2/2015 | Collingwood et al. |
| 8,956,828 | B2 | 2/2015 | Bonini et al. |
| 9,005,973 | B2 | 4/2015 | Cost et al. |
| 9,045,763 | B2 | 6/2015 | DeKelver et al. |
| 9,050,299 | B2 | 6/2015 | Bankiewicz |
| 9,089,667 | B2 | 7/2015 | Bankiewicz |
| 10,435,441 | B2 * | 10/2019 | Froelich ............. C07K 14/4703 |
| 2003/0232410 | A1 | 12/2003 | Liljedahl et al. |
| 2005/0026157 | A1 | 2/2005 | Baltimore et al. |
| 2005/0064474 | A1 | 3/2005 | Urnov et al. |
| 2005/0208489 | A1 | 9/2005 | Carroll et al. |
| 2006/0063231 | A1 | 3/2006 | Li et al. |
| 2006/0239966 | A1 | 10/2006 | Tornoe et al. |
| 2007/0283460 | A9 | 12/2007 | Liu et al. |
| 2008/0159996 | A1 | 7/2008 | Ando et al. |
| 2009/0068164 | A1 | 3/2009 | Segal et al. |
| 2009/0111119 | A1 | 4/2009 | Doyon et al. |
| 2010/0218264 | A1 | 8/2010 | Cui et al. |
| 2011/0082093 | A1 | 4/2011 | Gregory et al. |
| 2011/0265198 | A1 | 10/2011 | Gregory et al. |
| 2012/0017290 | A1 | 1/2012 | Cui et al. |
| 2012/0195936 | A1 | 8/2012 | Rudolph et al. |
| 2013/0122591 | A1 | 5/2013 | Cost et al. |
| 2013/0137104 | A1 | 5/2013 | Cost et al. |
| 2013/0177960 | A1 | 7/2013 | Rebar |
| 2013/0177983 | A1 | 7/2013 | Rebar |
| 2013/0196373 | A1 | 8/2013 | Gregory et al. |
| 2013/0253040 | A1 | 9/2013 | Miller et al. |
| 2013/0336947 | A1 | 12/2013 | Isalan et al. |
| 2014/0336133 | A1 | 11/2014 | Miller et al. |
| 2015/0056705 | A1 | 2/2015 | Conway et al. |
| 2015/0267205 | A1 | 9/2015 | Froelich et al. |
| 2015/0335708 | A1 | 11/2015 | Froelich et al. |

FOREIGN PATENT DOCUMENTS

| | | | |
|---|---|---|---|
| WO | WO 96/06166 | A1 | 2/1996 |
| WO | WO 98/53057 | A1 | 11/1998 |
| WO | WO 98/53058 | A1 | 11/1998 |
| WO | WO 98/53059 | A1 | 11/1998 |
| WO | WO 98/53060 | A1 | 11/1998 |
| WO | WO 98/54311 | A1 | 12/1998 |
| WO | WO 00/27878 | A1 | 5/2000 |
| WO | WO 01/60970 | A2 | 8/2001 |
| WO | WO 01/88197 | A2 | 11/2001 |
| WO | WO 02/16536 | A1 | 2/2002 |
| WO | WO 02/099084 | A2 | 12/2002 |
| WO | WO 03/016496 | A2 | 2/2003 |
| WO | WO 10/079430 | A1 | 7/2010 |
| WO | WO 2011/016840 | A2 | 2/2011 |
| WO | WO 2013/130824 | A1 | 9/2013 |
| WO | 2016183298 | A2 | 11/2016 |

OTHER PUBLICATIONS

An, et al., "Genetic Correction of Huntington's Disease Phenotypes in Induced Pluripotent Stem Cells," *Cell Stem Cell* 11(2):253-263 (2012).

Berardelli, et al. "Pathophysiology of Chorea and Bradykinesia in Huntington's Disease," *Movement Disorders* 14(3):398-403 (1999).

Beurdeley, et al., "Compact Designer Talens for Efficient Genome Engineering," *Nat Commun.* 4:1762 (2013).

Boch, et al., "Breaking the Code of DNA Binding Specificity of Tal-Type III Effectors," *Science* 326(5959):1509-1512 (2009).

Boissel, et al., "Megatals: A Rare-Cleaving Nuclease Architecture for Therapeutic Genome Engineering," *Nucl Acid Res:* 42(4):2591-601 (2014).

Bonas, et al., "Genetic and Structural Characterization of the Avirulence Gene AVRBS3 From Xanthomonas Campestris PV. Vesicatoria," *Mol. Gen. Genet.* 218(1):127-136 (1989).

Brouns, et al., "Small CRISPR RNAs Guide Antiviral Defense in Prokaryotes," *Science* 321:960-964 (2008).

Chae, et al., "Quantitative Proteomic Analysis of Induced Pluripo Pent Stem Cells Derived From a Human Huntington's Disease Patient," *Biochem J* 446(3):359-371 (2012).

Ciesielska, et al., "Anterograde Axonal Transport of AAV2-GDNF in Rat Basal Ganglia," *Molecular Therapy* 19(5):922-927 (2011).

Ciesielska, et al., "Cerebral Infusion of AAV9 Vector-Encoding Non-Self Proteins Can Elicit Cell-Mediated Immune Responses," *Mol Ther.* 21(1):158-166 (2013).

Cong, et al., "Multiplex Genome Engineering Using CRISPR/CAS Systems," *Science* 339(6121):819-23 (2013).

Davies, et al., "Polyalanine and Polyserine Frameshift Products in Huntington's Disease," *Journal of Medical Genetics* 43(11):893-896 (2006).

Di Prospero, et al., "Therapeutics Development for Triplet Repeat Expansion Diseases," *Nature Reviews Genetics* 6(10):756-765 (2005).

Esvelt, et al., "Orthogonal CAS9 Proteins for RNA-Guided Gene Regulation and Editing," *Nat. Meth.* 10(11):1116-21 (2013).

Fiandaca, et al., "Image-Guided Convection-Enhanced Delivery Platform in the Treatment of Neurological Diseases," *Neurotherapeutics* 5(1):123-127 (2008).

Fiandaca, et al. "Real-Time Mr Imaging of Adeno-Associated Viral Vector Delivery to the Primate Brain," *Neuroimage* 47 Suppl 2:T27-T35 (2009).

Fonfara, et al., "Phylogeny of CAS9 Determines Functional Exchange-ability of Dual-RNA and CAS9 Among Orthologous Type II CRISPR-CAS Systems," *Nuc. Acids Res.* 42(4):2577-2590 (2014).

Forsayeth, et al., "Transduction of Antigen-Presenting Cells in the Brain by AAV9 Warrants Caution in Preclinical Studies," *Mol Ther* 23(4):612 (2015).

Foust, et al. "Intravascular AAV9 Preferentially Targets Neonatal-Neurons and Adult-Astrocytes in CNS," *Nat Biotechnol* 27(1):59-65 (2009).

Garriga-Canut, et al. "Synthetic Zinc Finger Repressors Reduce Mutant Huntingtin Expression in the Brain of R6/2 Mice," *Proc Natl Acad Sci USA* 109(45):E3136-45 (2012).

Godde, et al., "The Repetitive DNA Elements Called CRISPRS and Their Associated Genes: Evidence of Horizontal Transfer Among Prokaryotes," *J. Mol. Evol.* 62(6):718-729 (2006).

Graham, et al., "Cleavage at the Caspase-6 Site Is Required for Neuronal Dysfunction and Degeneration Due to Mutant Huntingtin," *Cell* 125(6):1179-1191 (2006).

Gray, et al. "Preclinical Differences of Intravascular AAV9 Delivery to Neurons and Glia: A Comparative Study of Adult Mice and Nonhuman Primates," *Mol Ther* 19(6):1058-1069 (2011).

Hadaczek, et al. "The Perivascular Pump Driven by Arterial Pulsation Is a Powerful Mechanism for the Distribution of Therapeutic Molecules Within the Brain," *Mol Ther* 14(1):69-78 (2006).

Haft, et al., "A Guild of 45 CRISPR-Associated (CAS) Protein Families and Multiple CRISPR/CAS Subtypes Exist in Prokaryotic Genomes," *PLoS Comput. Biol.* 1(6):e60 (2005).

Hale, et al., "Prokaryotic Silencing (PSI)RNAs in *Pyrococcus furiosus,*" *RNA* 14(12):2572-2579 (2008).

Heuer, et al., "Repeat Domain Diversity of AVRBS3-Like Genes in Ralstonia Solanacearum Strains and Association With Host Preferences in the Field," *Appl. Envir. Microbiol.* 73(13):4379-4384 (2007).

Hinderer et al., "Widespread Gene Transfer in the Central Nervous System of Cynomolgus Macaques Following Delivery of AAV9 Into the Cisterna Magna," *Mol Ther Methods Clin Dev* 1:14051; doi:10.1038/mtm.2014.51 (2014).

Hsu, et al., "DNA Targeting Specificity of RNA-Guided CAS9 Nucleases," *Nat Biotechnol.* 31(9):827-832, doi: 10.1038/nbt.2647 (2013).

Huntington Study Group, "Unified Huntington's Disease Rating Scale (UHDRS) Reliability and Consistency," *Mov Disord.,* 11(2):136-142 (1996).

Hwang, et al., "Efficient In Vivo Genome Editing Using RNA-Guided Nucleases," *Nat Biotechnol.* 31(3):227-229 (2013).

(56) References Cited

OTHER PUBLICATIONS

Jansen, et al., "Identification of Genes That Are Associated With DNA Repeats in Prokaryotes," Mol Microbiol. 43(6):1565-1575 (2002).
Jinek, et al., "A Programmable Dual-RNA-Guided DNA Endonuclease in Adaptive Bacterial Immunity," Science 337(6096):816-821 (2012).
Kay, et al., "A Bacterial Effector Acts as a Plant Transcription Factor and Induces a Cell Size Regulator," Science 318(5850):648-651 (2007).
Kells, et al., "AAV-Mediated Gene Delivery of BDNF or GDNF Is Neuroprotective in a Model of Huntington Disease," Mol Ther 9(5):682-688 (2004).
Kells, et al., "Efficient Gene Therapy-Based Method for the Delivery of Therapeutics to Primate Cortex," Proc Natl Acad Sci USA 106(7):2407-2411 (2009).
Kells, et al., "Glial-Derived Neurotrophic Factor Gene Transfer for Parkinson'S Disease: Anterograde Distribution of AAV2 Vectors in the Primate Brain," Neurobiol Dis. 48(2):228-235 (2012).
Kormann, et al, Expression of Therapeutic Proteins After Delivry of Chemically Modified mRNA in Mice, Nat Biotechnol. 29(2):154-157 (2011).
Krauze, et al., "Reflux-Free Cannula for Convection-Enhanced High-Speed Delivery of Therapeutic Agents," J Neurosurg 103(5):923-929 (2005).
Lillestol, et al., "A Putative Viral Defence Mechanism in Archaeal Cells," Archaea 2(1):59-72 (2006).
Makarova, et al., "A DNA Repair System Specific for Thermophilic Archaea and Bacteria Predicted by Genomic Context Analysis," Nucleic Acids Res. 30(2):482-496 (2002).
Makarova, et al., "A Putative RNA-Interference-Based Immune System in Prokaryotes: Computational Analysis of the Predicted Enzymatic Machinery, Functional Analogies With Eukaryotic RNAI, and Hypothetical Mechanisms of Action," Biol. Direct 1:7 (2006).
Mattis, et al., "Induced Pluripotent Stem Cells From Patients With Huntington's Disease Show CAG Repeat Expansion Associated Phenotypes," Cell Stem Cell 11(2):264-278 (2012).
Moscou, et al., "A Simple Cipher Governs DNA Recognition by TAL Effectors," Science 326(5959):1501 (2009).
Niccolini, et al., "Altered PDE10A Expression Detectable Early Before Symptomatic Onset in Huntington's Disease," Brain 138(Pt 10):3016-3929 (2015).
Perez-Pinera, et al., "RNA-Guided Gene Activation by CRISPR-CAS9-Based Transcription Factors," Nat Methods 10(10):973-976 (2013).
Piatek, et al., "RNA-Guided Transcriptional Regulation in Planta via Synthetic DCAS9-Based Transcription Factors," Plant Biotechnology J. 13(4):578-589 (2015).
Richardson, et al., "Interventional MRI-Guided Putaminal Delivery of AAV2-GDNF for a Planned Clinical Trial in Parkinson's Disease," Mol Ther 19(6):1048-1057 (2011).
Richardson, et al. "Novel Platform for MRI-Guided Convection-Enhanced Delivery of Therapeutics: Preclinical Validation in Nonhuman Primate Brain," Stereotact Funct Neurosurg 89(3):141-151 (2011).
Russell, et al., "The Phosphodiesterase 10 Positron Emission Tomography Tracer, [18F]MNI-659, as a Novel Biomarker for Early Huntington Disease," JAMA Neurology 71(12):1520-1528 (2014).
Salegio, et al., "Axonal Transport of Adeno-Associated Viral Vectors Is Serotype-Dependent," Gene Ther. 20(3):348-352 (2013).
Samaranch, et al., "AAV9-Mediated Expression of a Non-Self Protein in Nonhuman Primate Cetral Nervous System Triggers Widespread Neuroinflammation Driven by Antigen-Presenting Cell Transduction," Mol Ther. 22(2):329-337 (2014).
San Sebastian, et al., "Adeno-Associated Virus Types 6 Is Retrogradely Transported in the Non-Human Primate Brain," Gene Ther. 20(12):1178-1183 (2013).
San Sebastian, et al., "Safety and Tolerability of MRI-Guided Infusion of AAV2-HAADC Into the Mid-Brain of Nonhuman Primate," Mol Ther Methods Clin Dev 3(pii):14049 (2014).
Sander, et al., "CRISPR-CAS Systems for Editing, Regulation and Targeting," Nat Biotechnol. 32(4):347-355 (2014).
Schornack, et al., "Gene-For-Gene-Mediated Recognition of Nuclear-Targeted AVRBS3-Like Bacterial Effector Proteins," J. Plant Physiol. 163(3):256-272 (2006).
Shen, et al.,"Terminal N-Linked Galactose Is the Primary Receptor for Adeno-Associated Virus 9," J Biol Chem 286(15):13532-13540 (2011).
Sheng, et al., "Structure-Based Cleavage Mechanism of Thermus Thermophilus Argonaute DNA Guide Strand-Mediated DNA Target Cleavage," Proc. Natl. Acad. Sci. USA 111(2):652-657 (2014).
Sorek, et al., "CRISPR—A Widespread System That Provides Acquired Resistance Against Phages in Bacteria and Archaea," Nat. Rev. Microbiol. 6(3):181-186 (2008).
Summerford, et al., "Membrane-Associated Heparan Sulfate Proteoglycan Is a Receptor for Adeno-Associated Virus Type 2 Virions," J Virol 72(2):1438-1445 (1998).
Swarts, et al., "DNA-Guided DNA Interference by a Prokaryotic Argonaute," Nature 507(7491):258-261 (2014).
Tang, et al., "Identification of Novel Non-Coding RNAs as Potential Antisense Regulators in the Archaeon Sulfolobus solfataricus," Mol. Microbiol. 55(2):469-481 (2005).
Tang, et al., "Identification of 86 Candidates for Small Non-Messenger RNAs From the Archaeon Archaeoglobus fulgidus," Proc Natl Acad Sci USA 99(11):7536-7541 (2002).
Walker, "Huntington's Disease," Lancet 369(9557):218-228 (2007).
White, et al., "Huntingtin Is Required for Neurogenesis and Is Not Impaired by the Huntington's Disease CAG Expansion," Nature Genetics 17(4):404-410 (1997).
Wild, et al., "Quantifying Mutant Huntingtin in Huntington's Disease CSF," J. Neurol. Neurosurg. Psychiatry 85:A6-A7, doi: 10.1136/jnnp-2014-309236.23 (2014).
Wu, et al., "Genome-Wide Binding of the CRISPR Endonuclease CAS9 in Mammalian Cells," Nature Biotech 32(7): 670-676, doi:10.1038/nbt2889 (2014).
Yu, et al., "An Engineered VEGF-Activating Zinc Finger Protein Transcription Factor Improves Blood Flow and Limb Salvage in Advanced-Age Mice," FASEB J. 20(3):479-481 (2006).
Zuccato, et al., "Progressive Loss of BDNF in a Mouse Model of Huntington's Disease and Rescue by BDNF Delivery," Pharmacol Res 52(2):133-139 (2005).

* cited by examiner

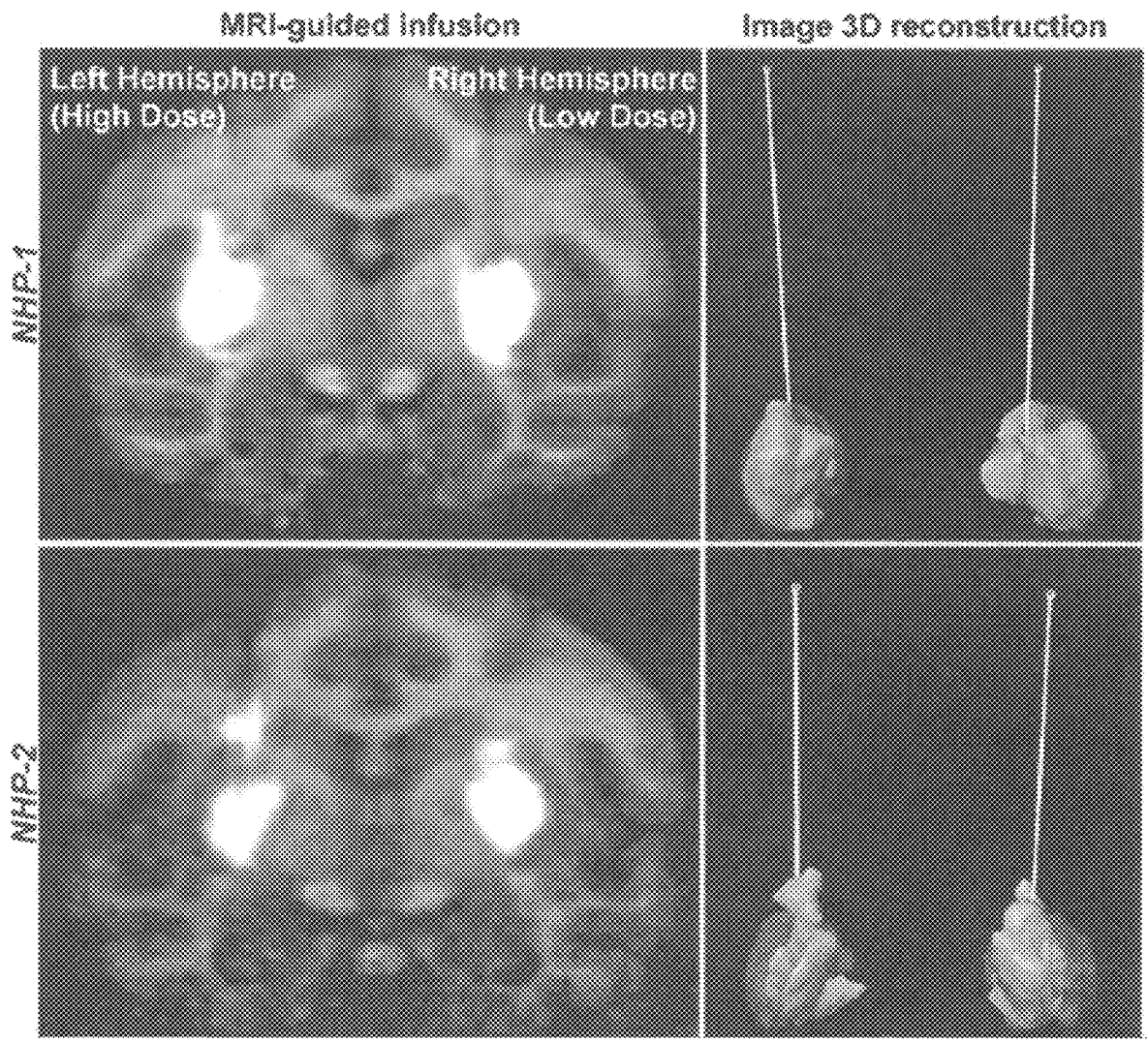

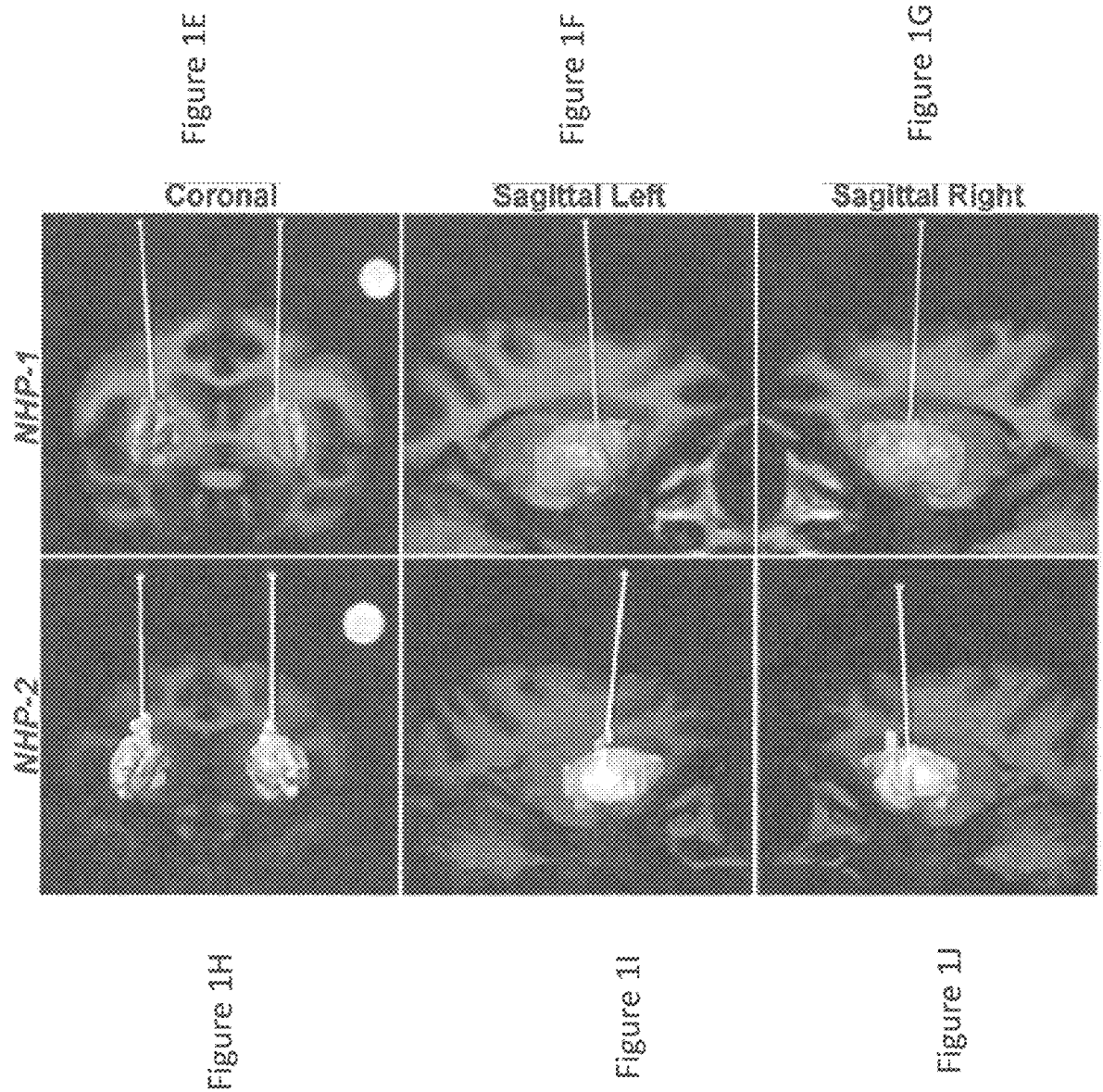

SEQUENCE LISTING

```
<160> NUMBER OF SEQ ID NOS: 6

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gln Ser Gly Asp Leu Thr Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys His Gly Asn Leu Ser Glu
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3
```

```
Lys Arg Cys Asn Leu Arg Cys
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Pro Ser His Leu Thr Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Gln Phe Asn Arg His Gln
1               5

<210> SEQ ID NO 6
<211> LENGTH: 28
<212> TYPE: DNA
<213> ORGANISM: Unknown
<220> FEATURE:
<223> OTHER INFORMATION: Description of Unknown:
      Human or mouse oligonucleotide

<400> SEQUENCE: 6
agcagcagca gcagcagcag cagcagca                                        28
```

HTT REPRESSORS AND USES THEREOF

CROSS-REFERENCE TO RELATED APPLICATIONS

The present application is a continuation of U.S. patent application Ser. No. 15/274,357, filed Sep. 23, 2016, which claims the benefit of U.S. Provisional Application No. 62/222,588, filed Sep. 23, 2015, the disclosure of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Aug. 19, 2019, is named 8325013901SL.txt and is 1,545 bytes in size.

TECHNICAL FIELD

The present disclosure is in the field of diagnostics and therapeutics for Huntington's Disease.

BACKGROUND

Huntington's Disease (HD), also known as Huntington's Chorea, is a progressive disorder of motor, cognitive and psychiatric disturbances. The mean age of onset for this disease is age 35-44 years, although in about 10% of cases, onset occurs prior to age 21, and the average lifespan post-diagnosis of the disease is 15-18 years. Prevalence is about 3 to 7 among 100,000 people of western European descent.

Huntington's Disease is an example of a trinucleotide repeat expansion disorders were first characterized in the early 1990s (see Di Prospero and Fischbeck (2005) *Nature Reviews Genetics* 6:756-765). These disorders involve the localized expansion of unstable repeats of sets of three nucleotides and can result in loss of function of the gene in which the expanded repeat resides, a gain of toxic function, or both. Trinucleotide repeats can be located in any part of the gene, including non-coding and coding gene regions. Repeats located within the coding regions typically involve either a repeated glutamine encoding triplet (CAG) or an alanine encoding triplet (CGA). Expanded repeat regions within non-coding sequences can lead to aberrant expression of the gene while expanded repeats within coding regions (also known as codon reiteration disorders) may cause mis-folding and protein aggregation. The exact cause of the pathophysiology associated with the aberrant proteins is often not known. Typically, in the wild-type genes that are subject to trinucleotide expansion, these regions contain a variable number of repeat sequences in the normal population, but in the afflicted populations, the number of repeats can increase from a doubling to a log order increase in the number of repeats. In HD, repeats are inserted within the N terminal coding region of the large cytosolic protein Huntingtin (Htt). Normal Htt alleles contain 15-20 CAG repeats, while alleles containing 35 or more repeats can be considered potentially HD causing alleles and confer risk for developing the disease. Alleles containing 36-39 repeats are considered incompletely penetrant, and those individuals harboring those alleles may or may not develop the disease (or may develop symptoms later in life) while alleles containing 40 repeats or more are considered completely penetrant. In fact, no asymptomatic persons containing HD alleles with this many repeats have been reported. Those individuals with juvenile onset HD (<21 years of age) are often found to have 60 or more CAG repeats. In addition to an increase in CAG repeats, it has also been shown that HD can involve +1 and +2 frameshifts within the repeat sequences such that the region will encode a poly-serine polypeptide (encoded by AGC repeats in the case of a +1 frameshift) track rather than poly-glutamine (Davies and Rubinsztein (2006) *Journal of Medical Genetics* 43: 893-896).

In HD, the mutant Htt allele is usually inherited from one parent as a dominant trait. Any child born of a HD patient has a 50% chance of developing the disease if the other parent was not afflicted with the disorder. In some cases, a parent may have an intermediate HD allele and be asymptomatic while, due to repeat expansion, the child manifests the disease. In addition, the HD allele can also display a phenomenon known as anticipation wherein increasing severity or decreasing age of onset is observed over several generations due to the unstable nature of the repeat region during spermatogenesis.

Furthermore, trinucleotide expansion in Htt leads to neuronal loss in the medium spiny gamma-aminobutyric acid (GABA) projection neurons in the striatum, with neuronal loss also occurring in the neocortex. Medium spiny neurons that contain enkephalin and that project to the external globus pallidum are more involved than neurons that contain substance P and project to the internal globus pallidum. Other brain areas greatly affected in people with Huntington's disease include the substantia nigra, cortical layers 3, 5, and 6, the CA1 region of the hippocampus, the angular gyms in the parietal lobe, Purkinje cells of the cerebellum, lateral tuberal nuclei of the hypothalamus, and the centromedialparafascicular complex of the thalamus (Walker (2007) *Lancet* 369:218-228).

The role of the normal Htt protein is poorly understood, but it may be involved in neurogenesis, apoptotic cell death, and vesicle trafficking. In addition, there is evidence that wild-type Htt stimulates the production of brain-derived neurotrophic factor (BDNF), a pro-survival factor for the striatal neurons. It has been shown that progression of HD correlates with a decrease in BDNF expression in mouse models of HD (Zuccato et al. (2005) *Pharmacological Research* 52(2):133-139), and that delivery of either BDNF or glial cell line-derived neurotrophic factor (GDNF) via adeno-associated viral (AAV) vector-mediated gene delivery may protect straital neurons in mouse models of HD (Kells et al. (2004) *Molecular Therapy* 9(5):682-688).

Diagnostic and treatment options for HD are currently very limited. In terms of diagnostics, altered (mutant) Htt (mHTT) levels are significantly associated with disease burden score, and soluble mHTT species increase in concentration with disease progression. However, low-abundance mHTT is difficult to quantify in the patient CNS, which limits both study of the role in the neuropathobiology of HD in vivo, and precludes the demonstration of target engagement by HTT-lowering drugs. See, e.g., Wild et al. (2014) *J Neurol Neurosurg Psychiatry* 85:e4.

With regard to treatment, some potential methodologies designed to prevent the toxicities associated with protein aggregation that occurs through the extended poly-glutamine tract such as overexpression of chaperonins or induction of the heat shock response with the compound geldanamycin have shown a reduction in these toxicities in in vitro models. Other treatments target the role of apoptosis in the clinical manifestations of the disease. For example, slowing of disease symptoms has been shown via blockage of caspase activity in animal models in the offspring of a pairing of mice where one parent contained a HD allele and the other parent had a dominant negative allele for caspase 1. Additionally, cleavage of mutant HD Htt by caspase may play a role in the pathogenicity of the disease. Transgenic mice carrying caspase-6 resistant mutant Htt were found to maintain normal neuronal function and did not develop striatal neurodegeneration as compared to mice carrying a non-caspase resistant mutant Htt allele (see Graham et al. (2006) *Cell* 125: 1179-1191). Molecules which target members of the apoptotic pathway have also been shown to have a slowing effect on symptomology. For example, the compounds zVAD-fmk and minocycline, both of which inhibit caspase activity, have been shown to slow disease manifestation in mice. The drug remacemide has also been used in small HD human trials because the compound was thought to prevent the binding of the mutant Htt to the NDMA receptor to prevent the exertion of toxic effects on the nerve cell. However, no statistically significant improvements were observed in neuron function in these trials. In addition, the Huntington Study Group conducted a randomized, double-blind study using Coenzyme Q. Although a trend towards slower disease progression among patients that were treated with coenzyme Q10 was observed, there was no significant change in the rate of decline of total functional capacity. (Di Prospero and Fischbeck, ibid).

Recombinant transcription factors and nucleases comprising the DNA binding domains from zinc finger proteins ("ZFPs"), TAL-effector domains ("TALEs") and CRISPR/Cas transcription factor systems (including Cas and/or Cfp1 systems) have the ability to regulate gene expression of endogenous genes. See, e.g., U.S. Pat. Nos. 9,045,763; 9,005,973; 8,956,828; 8,945,868; 8,586,526; 6,534,261; 6,599,692; 6,503,717; 6,689,558; 7,067,317; 7,262,054; 7,888,121; 7,972,854; 7,914,796; 7,951,925; 8,110,379; and 8,409,861; U.S. Patent Publication Nos. 2003/0232410; 2005/0208489; 2005/0026157; 2006/0063231; 2008/0159996; 2010/00218264; 2012/0017290; 2011/0265198; 2013/0137104; 2013/0122591; 2013/0177983; 2013/0177960; 2015/0056705; and 2015/0335708; Perez-Pinera et al. (2013) *Nature Methods* 10:973-976; Piatek et al. (2014) *Plant Biotechnology J.* doi: 10.1111/pbi.12284), the disclosures of which are incorporated by reference in their entireties for all purposes. Further, targeted nucleases are being developed based on the Argonaute system (e.g., from *T. thermophilus*, known as 'TtAgo', see Swarts et al. (2014) *Nature* 507(7491):258-261), which also may have the potential for uses in genome editing and gene therapy. Clinical trials using these engineered transcription factors containing zinc finger proteins have shown that these novel transcription factors are capable of treating various conditions. (see, e.g., Yu et al. (2006) *FASEB J.* 20:479-481). Nuclease-mediated cleavage involves the use of engineered nucleases to induce a double strand break (DSB) or a nick in a target DNA sequence such that repair of the break by an error born process such as non-homologous end joining (NHEJ) or repair using a repair template (homology directed repair or HDR) can result in the knock out of a gene or the insertion of a sequence of interest (targeted integration). Introduction of a double strand break in the absence of an externally supplied repair template (e.g. "donor" or "transgene") is commonly used for the inactivation of the targeted gene via mutations (insertions and/or deletions known as "indels") introduced by the cellular NHEJ pathway. For instance, U.S. Patent Publication No. 2011/0082093 discloses specific zinc finger proteins targeted to Htt and U.S. Patent Publication No. 2013/0253040 relates to DNA-binding proteins that modulate expression of an HD allele such as Htt. U.S. Patent Publication No. 2015/0335708 relates to methods of modifying medium spiny neurons.

However, there remains a need for methods for the diagnosis, study, treatment and/or prevention of Huntington's Disease, including for modalities that exhibit widespread delivery to the brain.

SUMMARY

Disclosed herein are methods and compositions for diagnosing, preventing and/or treating Huntington's Disease. In particular, provided herein are methods and compositions for modifying (e.g., modulating expression of) an HD Htt allele so as to treat Huntington Disease, including Htt repressors (that repress Htt expression). The compositions (Htt repressors) described herein provide a therapeutic benefit in subjects, for example by reducing cell death, decreasing apoptosis, increasing cellular function (metabolism) and/or reducing motor deficiency in the subjects. Also provided are methods and compositions that allow for bi-directional axonal transport in a primate brain. Surprisingly and unexpectedly, the present inventors have found that unlike other AAV serotypes that have been used, AAV9 exhibits widespread delivery throughout the brain, including anterograde and retrograde axonal transport to brain regions distant from the site of AAV9 administration. Thus, described herein is a non-naturally occurring zinc finger protein that binds to an Htt gene, the zinc finger protein comprising 5 zinc finger domains ordered F1 to F5, wherein the zinc finger domains comprise the recognition helix regions sequences shown in a single row of Table 1.

Thus, in one aspect, engineered (non-naturally occurring) Htt repressors are provided. The repressors may comprise systems (e.g., zinc finger proteins, TAL effector (TALE) proteins or CRISPR/dCas-TF) that modulate expression of a HD allele (e.g., Htt). Engineered zinc finger proteins or TALEs are non-naturally occurring zinc finger or TALE proteins whose DNA binding domains (e.g., recognition helices or RVDs) have been altered (e.g., by selection and/or rational design) to bind to a pre-selected target site. Any of the zinc finger proteins described herein may include 1, 2, 3, 4, 5, 6 or more zinc fingers, each zinc finger having a recognition helix that binds to a target subsite in the selected sequence(s) (e.g., gene(s)). Similarly, any of the TALE proteins described herein may include any number of TALE RVDs. In some embodiments, at least one RVD has non-specific DNA binding. In some embodiments, at least one recognition helix (or RVD) is non-naturally occurring. In certain embodiments, the zinc finger proteins have the recognition helices in the proteins designated 45643 or 46025 (Table 1). In certain embodiments, the repressor comprises a DNA-binding domain (ZFP, TALE, single guide RNA) operably linked to a transcriptional repression domain. In some embodiments these ZFP-TFs, CRISPR/dCas-TFs or TALE-TFs include protein interaction domains (or "dimerization domains") that allow multimerization when bound to DNA.

In certain embodiments, the zinc finger proteins (ZFPs), Cas protein of a CRISPR/Cas system or TALE proteins as described herein can be placed in operative linkage with a regulatory domain (or functional domain) as part of a fusion protein. The functional domain can be, for example, a transcriptional activation domain, a transcriptional repression domain and/or a nuclease (cleavage) domain. By selecting either an activation domain or repression domain for use with the DNA-binding domain, such molecules can be used either to activate or to repress gene expression. In some embodiments, a molecule comprising a ZFP, dCas or TALE targeted to a mutant Htt as described herein fused to a transcriptional repression domain that can be used to down-regulate mutant Htt expression is provided. In some embodiments, a fusion protein comprising a ZFP, CRISPR/Cas or TALE targeted to a wild-type Htt allele fused to a transcription activation domain that can up-regulate the wild type Htt allele is provided. In certain embodiments, the activity of the regulatory domain is regulated by an exogenous small molecule or ligand such that interaction with the cell's transcription machinery will not take place in the absence of the exogenous ligand, while in other embodiments, the exogenous small molecule or ligand prevents the interaction. Such external ligands control the degree of interaction of the ZFP-TF, CRISPR/Cas-TF or TALE-TF with the transcription machinery. The regulatory domain(s) may be operatively linked to any portion(s) of one or more of the ZFPs. dCas or TALEs, including between one or more ZFPs, dCas or TALEs, exterior to one or more ZFPs, dCas or TALEs and any combination thereof. Any of the fusion proteins described herein may be formulated into a pharmaceutical composition.

In some embodiments, the engineered DNA binding domains as described herein can be placed in operative linkage with nuclease (cleavage) domains as part of a fusion protein. In some embodiments, the nuclease comprises a Ttago nuclease. In other embodiments, nuclease systems such as the CRISPR/Cas system may be utilized with a specific single guide RNA to target the nuclease to a target location in the DNA. In certain embodiments, such nucleases and nuclease fusions may be utilized for targeting mutant Htt alleles in stem cells such as induced pluripotent stem cells (iPSC), human embryonic stem cells (hESC), mesenchymal stem cells (MSC) or neuronal stem cells wherein the activity of the nuclease fusion will result in an Htt allele containing a wild type number of CAG repeats. Thus, any of the Htt repressors described herein can further comprise a dimerization domain and/or a functional domain (e.g., transcriptional activation domain, a transcriptional repression domain or a nuclease domain). In certain embodiments, pharmaceutical compositions comprising the modified cells (e.g., stem cells) are provided.

In yet another aspect, a polynucleotide encoding one or more of the DNA binding proteins described herein is provided. In certain embodiments, the polynucleotide is carried on a viral (e.g., AAV or Ad) vector and/or a non-viral (e.g., plasmid or mRNA vector). Host cells comprising these polynucleotides (e.g., AAV vectors) and/or pharmaceutical compositions comprising the polynucleotides, proteins and/or host cells as described herein are also provided.

In other aspects, the invention comprises delivery of a donor nucleic acid to a target cell. The donor may be delivered prior to, after, or along with the nucleic acid encoding the nuclease(s). The donor nucleic acid may comprise an exogenous sequence (transgene) to be integrated into the genome of the cell, for example, an endogenous locus. In some embodiments, the donor may comprise a full length gene or fragment thereof flanked by regions of homology with the targeted cleavage site. In some embodiments, the donor lacks homologous regions and is integrated into a target locus through homology independent mechanism (i.e. NHEJ). The donor may comprise any nucleic acid sequence, for example a nucleic acid that, when used as a substrate for homology-directed repair of the nuclease-induced double-strand break, leads to a donor-specified deletion to be generated at the endogenous chromosomal locus or, alternatively (or in addition to), novel allelic forms of (e.g., point mutations that ablate a transcription factor binding site) the endogenous locus to be created. In some aspects, the donor nucleic acid is an oligonucleotide wherein integration leads to a gene correction event, or a targeted deletion.

In some embodiments, the polynucleotide encoding the DNA binding protein is an mRNA. In some aspects, the mRNA may be chemically modified (See e.g. Kormann et al. (2011) *Nature Biotechnology* 29(2):154-157). In other aspects, the mRNA may comprise an ARCA cap (see U.S. Pat. Nos. 7,074,596 and 8,153,773). In further embodiments, the mRNA may comprise a mixture of unmodified and modified nucleotides (see U.S. Patent Publication No. 2012/0195936).

In yet another aspect, a gene delivery vector comprising any of the polynucleotides described herein is provided. In certain embodiments, the vector is an adenovirus vector (e.g., an Ad5/F35 vector), a lentiviral vector (LV) including integration competent or integration-defective lentiviral vectors, or an adenovirus associated viral vector (AAV). In certain embodiments, the AAV vector is an AAV6 or AAV9 vector. Thus, also provided herein are adenovirus (Ad) vectors, LV or adenovirus associate viral vectors (AAV) comprising a sequence encoding at least one nuclease (ZFN or TALEN) and/or a donor sequence for targeted integration into a target gene. In certain embodiments, the Ad vector is a chimeric Ad vector, for example an Ad5/F35 vector. In certain embodiments, the lentiviral vector is an integrase-defective lentiviral vector (IDLV) or an integration competent lentiviral vector. In certain embodiments the vector is pseudo-typed with a VSV-G envelope, or with other envelopes.

Additionally, pharmaceutical compositions comprising the nucleic acids and/or proteins (e.g., ZFPs, Cas or TALEs or fusion proteins comprising the ZFPs, Cas or TALEs) are also provided. For example, certain compositions include a nucleic acid comprising a sequence that encodes one of the ZFPs, Cas or TALEs described herein operably linked to a regulatory sequence, combined with a pharmaceutically acceptable carrier or diluent, wherein the regulatory sequence allows for expression of the nucleic acid in a cell. In certain embodiments, the ZFPs, CRISPR/Cas or TALEs encoded are specific for a HD Htt allele. In some embodiments, pharmaceutical compositions comprise ZFPs, CRISPR/Cas or TALEs that modulate a HD Htt allele and ZFPs, CRISPR/Cas or TALEs that modulate a neurotrophic factor. Protein based compositions include one of more ZFPs. CRISPR/Cas or TALEs as disclosed herein and a pharmaceutically acceptable carrier or diluent.

In yet another aspect also provided is an isolated cell comprising any of the proteins, polynucleotides and/or compositions as described herein.

In another aspect, described herein are methods of modifying expression of an Htt gene in a cell (e.g., neuronal cell in vitro or in vivo in a brain of a subject, e.g., the striatum), the method comprising administering to the cell one or more proteins, polynucleotides and/or cells as described herein. The Htt gene may comprise at least one wild-type and/or mutant Htt allele. In certain embodiments, Htt expression is repressed.

In another aspect, provided herein are methods for treating and/or preventing Huntington's Disease using the methods and compositions (proteins, polynucleotides and/or cells) described herein. In some embodiments, the methods involve compositions where the polynucleotides and/or proteins may be delivered using a viral vector, a non-viral vector (e.g., plasmid) and/or combinations thereof. In some embodiments, the methods involve compositions comprising stem cell populations comprising a ZFP or TALE, or altered with the ZFNs, TALENs, Ttago or the CRISPR/Cas nuclease system of the invention. The subject may comprise at least one mutant and/or wild-type Htt allele.

In a still further aspect, described here is a method of delivering a repressor of Htt to the brain of the subject using an AAV (e.g., AAV9) vector. Delivery may be to any brain region, for example, the striatum (e.g., putamen) by any suitable means including via the use of a cannula. In some embodiments, delivery is through direct injection into the intrathecal space. In further embodiments, delivery in through intravenous injection. The AAV9 vector provides widespread delivery of the repressor to brain of the subject, including via anterograde and retrograde axonal transport to brain regions not directly administered the vector (e.g., delivery to the putamen results in delivery to other structures such as the cortex, substantia nigra, thalamus, etc. In certain embodiments, the subject is a human and in other embodiments, the subject is a non-human primate.

Thus, in other aspects, described herein is a method of preventing and/or treating HD in a subject, the method comprising administering a repressor of a mutant Htt allele to the subject. The repressor may be administered in polynucleotide form (e.g., using a viral (e.g., AAV) and/or non-viral vector (e.g., plasmid and/or mRNA), in protein form and/or via a pharmaceutical composition as described herein (e.g., a pharmaceutical compositions comprising a polynucleotide, AAV vector, protein and/or cell as described herein). In certain embodiments, the repressor is administered to the CNS (e.g., putamen) of the subject. The repressor may provide therapeutic benefits, including, but not limited to, reducing the formation of Htt aggregates in HD neurons of a subject with HD; reducing cell death in a neuron or population of neurons (e.g., an HD neuron or population of HD neurons); and/or reducing motor deficits (e.g., clasping) in HD subjects.

In any of the methods described herein, the repressor of the mutant Htt allele may be a ZFP-TF, for example a fusion protein comprising a ZFP that binds specifically to a mutant Htt allele and a transcriptional repression domain (e.g., KOX, KRAB, etc.). In other embodiments, the repressor of the mutant Htt allele may be a TALE-TF, for example a fusion protein comprising a TALE polypeptide that binds specifically to a mutant Htt allele and a transcriptional repression domain (e.g., KOX, KRAB, etc.). In some embodiments, the mutant Htt allele repressor is a CRISPR/Cas-TF where the nuclease domains in the Cas protein have been inactivated such that the protein no longer cleaves DNA. The resultant Cas RNA-guided DNA binding domain is fused to a transcription repressor (e.g. KOX, KRAB etc.) to repress the mutant Htt allele. In still further embodiments, the repressor may comprise a nuclease (e.g., ZFN, TALEN and/or CRISPR/Cas system) that represses the mutant Htt allele by cleaving and thereby inactivating the mutant Htt allele. In certain embodiments, the nuclease introduces an insertion and/or deletion ("indel") via non-homologous end joining (NHEJ) following cleavage by the nuclease. In other embodiments, the nuclease introduces a donor sequence (by homology or non-homology directed methods), in which the donor integration inactivates the mutant Htt allele.

In any of the methods described herein, the repressor may be delivered to the subject (e.g., brain) as a protein, polynucleotide or any combination of protein and polynucleotide. In certain embodiments, the repressor(s) is(are) delivered using an AAV (e.g., AAV9) vector. In other embodiments, at least one component of the repressor (e.g., sgRNA of a CRISPR/Cas system) is delivered as in RNA form. In other embodiments, the repressor(s) is(are) delivered using a combination of any of the expression constructs described herein, for example one repressor (or portion thereof) on one expression construct (e.g., AAV such as AAV9) and one repressor (or portion thereof) on a separate expression construct (AAV or other viral or non-viral construct).

Furthermore, in any of the methods described herein, the repressors can be delivered at any concentration (dose) that provides the desired effect. In preferred embodiments, the repressor is delivered using an adeno-associated virus vector at 10,000-500,000 vector genome/cell (or any value therebetween). In certain embodiments, the repressor is delivered using a lentiviral vector at MOI between 250 and 1,000 (or any value therebetween). In other embodiments, the repressor is delivered using a plasmid vector at 150-1,500 ng/100,000 cells (or any value therebetween). In other embodiments, the repressor is delivered as mRNA at 150-1,500 ng/100,000 cells (or any value therebetween).

In any of the methods described herein, the method can yield about 70% or greater, about 75% or greater, about 85% or greater, about 90% or greater, about 92% or greater, or about 95% or greater repression of the mutant Htt alleles in one or more HD neurons of the subject.

In further aspects, the invention described herein comprises one or more Htt-modulating transcription factors, such as a Htt-modulating transcription factors comprising one or more of a zinc finger protein (ZFP TFs), a TALEs (TALE-TF), and a CRISPR/Cas-TFs for example, ZFP-TFs, TALE-TFs or CRISPR/Cas-TFs. In certain embodiments, the Htt-modulating transcription factor can repress expression of a mutant Htt allele in one or more HD neurons of a subject. The repression can be about 70% or greater, about 75% or greater, about 85% or greater, about 90% or greater, about 92% or greater, or about 95% or greater repression of the mutant Htt alleles in the one or more HD neurons of the subject as compared to untreated (wild-type) neurons of the subject. In certain embodiments, the Htt-modulating transcription factor can be used to achieve one or more of the methods described herein.

In some embodiments, therapeutic efficacy is measured using the Unified Huntington's Disease Rating Scale (UHDRS) (Huntington Study Group (1996)*Mov Disord* 11(2):136-142) for analysis of overt clinical symptoms. In other embodiments, efficacy in patients is measured using PET and MRI imaging. In some embodiments, treatment with the mutant Htt modulating transcription factor prevents any further development of overt clinical symptoms and prevents any further loss of neuron functionality. In other embodiments, treatment with the mutant Htt modulating transcription factor improves clinical symptoms and improves neuron function.

Also provided is a kit comprising one or more of the AAV9 Htt-modulators (e.g., repressors) and/or polynucleotides comprising components of and/or encoding the Htt-modulators (or components thereof) as described herein. The kits may further comprise cells (e.g., neurons), reagents (e.g., for detecting and/or quantifying mHtt protein, for example in CSF) and/or instructions for use, including the methods as described herein.

Thus, the present disclosure encompasses, but is not limited to, the following numbered embodiments:

1. A non-naturally occurring zinc finger protein that binds to an Htt gene, the zinc finger protein comprising 5 zinc finger domains ordered F1 to F5, wherein the zinc finger domains comprise the recognition helix regions sequences shown in a single row of Table 1.

2. The Htt repressor of 1, further comprising a dimerization domain that allows multimerization of zinc finger proteins when bound to DNA.

3. A fusion protein comprising a zinc finger protein of 1 or 2 and a functional domain.

4. The fusion protein of 3, wherein the functional domain is selected from the group consisting of a transcriptional activation domain, a transcriptional repression domain, and a nuclease domain.

5. A polynucleotide encoding one or more zinc finger proteins of 1 to 2 or one or more fusion proteins of 3 or 4.

6. An AAV vector comprising the polynucleotide of 5.

7. The AAV vector of 6, wherein the vector is an AAV9 vector.

8. A host cell comprising one or more zinc finger proteins of 1 to 2 or one or more fusion proteins of 3 or 4, one or more polynucleotides according to 5 or one or more AAV vectors according to 6 or 7.

9. A pharmaceutical composition comprising one or more zinc finger proteins of 1 to 2 or one or more fusion proteins of 3 or 4, one or more polynucleotides according to claim 5 or one or more AAV vectors according to 6 or 7.

10. A method of modifying expression of an Htt gene in a cell, the method comprising administering to the cell one or more polynucleotides according to 5 or one or more AAV vectors according to 6 or 7.

11. The method of 10, wherein the Htt gene comprises at least one mutant allele.

12. The method of 10, wherein the Htt gene is wild-type.

13. The method of any of 10 to 12, wherein the fusion protein comprises a repression domain and expression of the Htt gene is repressed.

14. The method of any of 10 to 13, wherein the cell is a neuronal cell.

15. The method of 14 wherein the neuronal cell is in a brain.

16. The method of 15, wherein the neuronal cell is in the striatum of the brain.

17. A method of treating and/or preventing Huntington's Disease in a subject in need thereof, the method comprising administering one or more polynucleotides according to 5 or one or more AAV vectors according to 6 or 7 to the subject in need thereof.

18. A method of modifying expression of an Htt gene in a cell, the method comprising administering to the cell one or more AAV9 vectors, the AAV9 vectors encoding one or more Htt repressors.

19. The method of 18, wherein the Htt gene comprises at least one mutant allele.

20. The method of 18, wherein the Htt gene is wild-type.

21. The method of any of 18 to 21, wherein the fusion protein comprises a repression domain and expression of the Htt gene is repressed.

22. The method of any of 18 to 21, wherein the cell is a neuronal cell.

23. The method of 22, wherein the neuronal cell is in a brain.

24. The method of 23, wherein the neuronal cell is in the striatum of the brain.

25. A method of treating and/or preventing Huntington's Disease in a subject in need thereof, the method comprising administering to the subject in need thereof one or more AAV9 vectors, the AAV9 vectors encoding one or more Htt repressors.

These and other aspects will be readily apparent to the skilled artisan in light of disclosure as a whole.

BRIEF DESCRIPTION OF THE DRAWINGS

FIGS. 1A through 1J are images depicting results following infusion of AAV9 vectors into NHP putamen. Comparative panels for the MRI-guided infusion of AAV9-GFP (100 µL) into the bilateral putamen of 2 normal nonhuman primates (designated NHP-1 and NHP-2) are shown in FIGS. 1A and 1B and 3 dimensional reconstructs of each subject are shown in FIGS. 1C and 1D. Reconstructed volumes for each putamen (n=4), labeled in blue measured approximately 850 µL for NHP-1 and 625 µL of NHP-2. The infusate containing AAV9-GFT particles and chelated gadolinium imaging reagent, labeled in orange, distributed into approximately 350 µL for each infusion. FIGS. 1E, 1F and 1G show coronal, sagittal left and sagittal right views (respectively) of cannula trajectory paths of NHP-1 and FIGS. 1H, 1I and 1J show coronal, sagittal left and sagittal right views (respectively) of cannula trajectory paths for NHP-2.

FIGS. 2A and 2B show GFP staining within the putamen. High magnification images of the boxed areas are shown below and depict NeuN-positive cells in putamen administered either a high dose ("HD", left hemisphere $1.5 \times 10^{13}$ vg/mL) or low dose ("LD", right hemisphere, 1.5 and $10^{12}$ vg/mL) of vector. FIGS. 2C and 2D are graphs depicting the primary area of transduction (PAT) shown in white and the area within the putamen "outside" the GFP-positive signal is "oPAT" and shown in grey. Counts of NeuN-positive cells in three coronal plants at PAT and oPAT, performed alongside naive control NHPs within the putamen showed no detectable difference in NeuN signal when the low and high dose hemispheres were compared. Counts of co-localized GFP-positive/NeuN-positive cells revealed transduction is about 74% efficient in PAT with low to null efficiency in oPAT. Data are represented as mean number of cells±SD. P-values (*) of <0.01 for transduced cells within PAT and oPAT, Wilcoxon sign-ranked S test. Scale bars for FIGS. 2A through 2D: 50 µM. FIGS. 2E, 2F, 2G and 2H show distal (FIGS. 2E and 2F) and proximal (FIGS. 2G and 2H) comparison of innate immune status. The up-regulation of positively stained MHCII (FIGS. 2E and 2G, scale bar of 50 µm) and Iba1 activation (FIGS. 2F and 2H, scale bar of 200 µm) is shown proximal to the site of infusion in comparison to the distal site.

FIGS. 3A, 3B and 3C show results in NHP-1 and FIGS. 3D, 3E and 3F show results in NHP-2. Double-label immunofluorescence revealed GFP expression in both NeuN-positive and GFAP-positive cell bodies. In contrast, capsids did not transduce Iba1-positive cell bodies, indicating the AAV9 does not appear to transduce microglia. Scale bars: 50 µm.

FIG. 5A shows results from NHP-1 and FIG. 5B shows results from NHP-2. The infusion of AAV9 into the putamen resulted in GFP-positive cells in many distal regions known to receive effects from the putamen. Shown is the anti-GFP immunohistochemistry with approximate position of each coronal section 12 mm posterior to the cannula tract. High magnification images below correspond to left and right hemispheres of the globus pallidus ("GP"), thalamus, subthalamic nucleaus ("STN"), medial forebrain bundle ("MFB") and substantia nigra ("SN"). Scale bars: 500 µM.

FIG. 6A depicts results in NHP-1 and FIG. 6B depicts results in NHP-2. Double-label immunofluorescence (yellow) is visible for GFP-positive (green) and tyrosine hydroxylase-positive (red) cell codies and fibers of the substantia nigra pars compacta ("Snc") and in fibers of the parts reticulata ("SNr"). Tyrosine hydroxylase ("TH") staining identifies dopaminergic neurons. Transduction of cell bodies in the SNr and SNc demonstrates both anterograde and retrograde axonal transport respectively. Increased expression of GFP was observed between the ipsilateral (high-dose) and contralateral (low-dose) hemispheres. Scale bars: 500 µm.

FIG. 12A demonstrates that ATP levels in the neurons are higher in the HD neurons treated with the ZFPs than in the cells treated with the VENUS control or the mock treated cells. In comparison, the wild type neurons do not show any effect from the ZFP treatment. FIG. 12B shows the percent of cells that are TUNEL positive (a marker for apoptosis), and demonstrates that the HD neurons treated with the ZFPs have less numbers of TUNEL positive cells than the control samples. For comparison, the graph also depicts the data from wild type neurons.

DETAILED DESCRIPTION

Figure 2A:
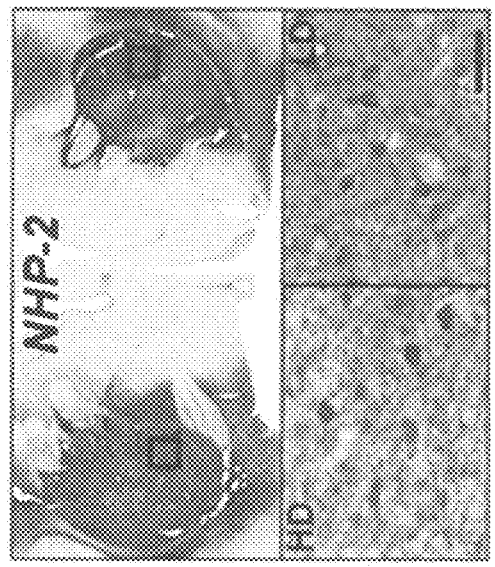
FIGS. 2A through 2H show AAV9-mediated GFP expression in the putamen of NHPs and innate immune status.
Figure 2B:
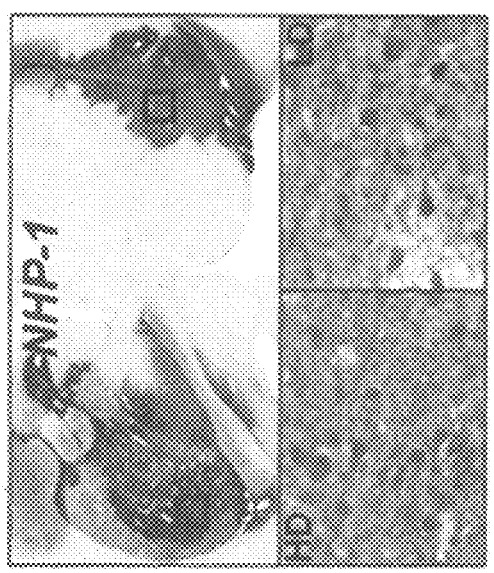
Figure 2C:
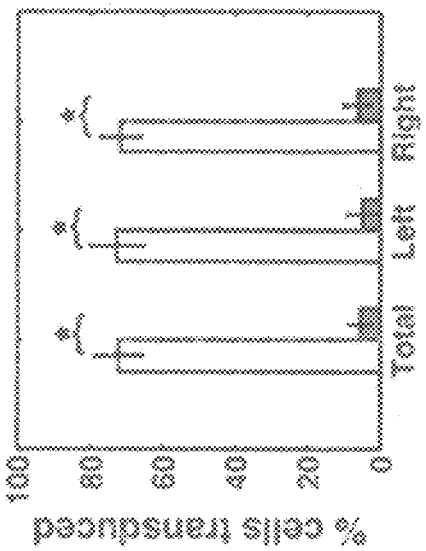
Figure 2D:
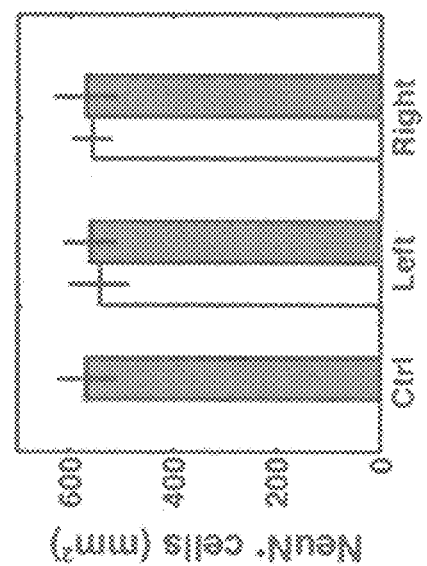
Figure 2F:
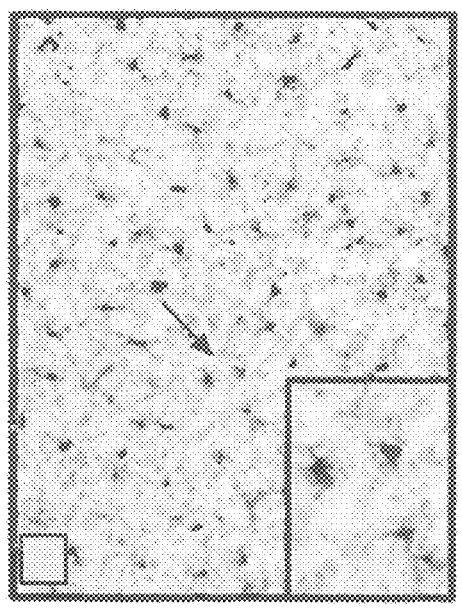
Figure 2H:
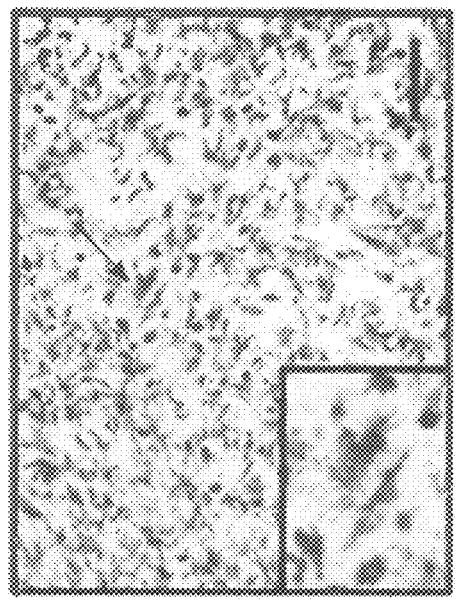
Figure 2E:
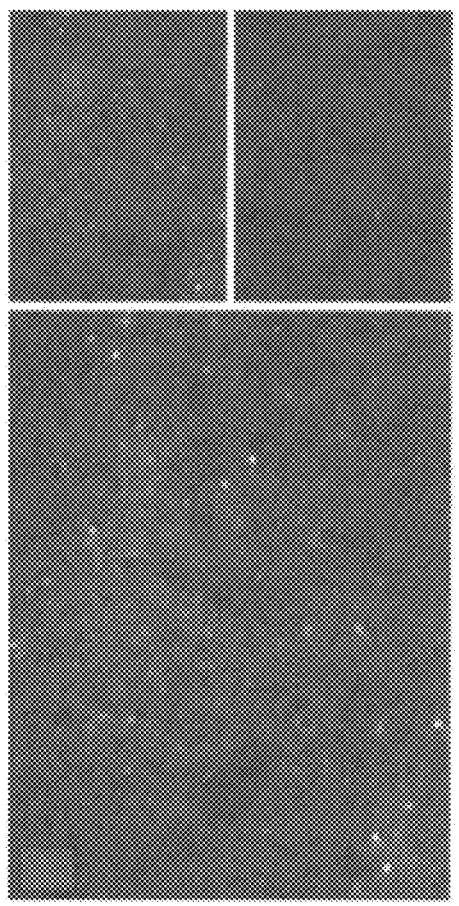
Figure 2G:
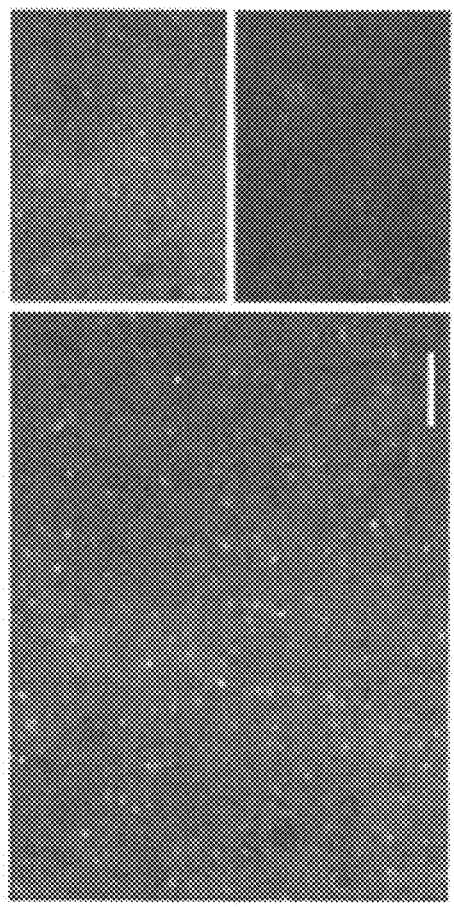
Figure 3A:
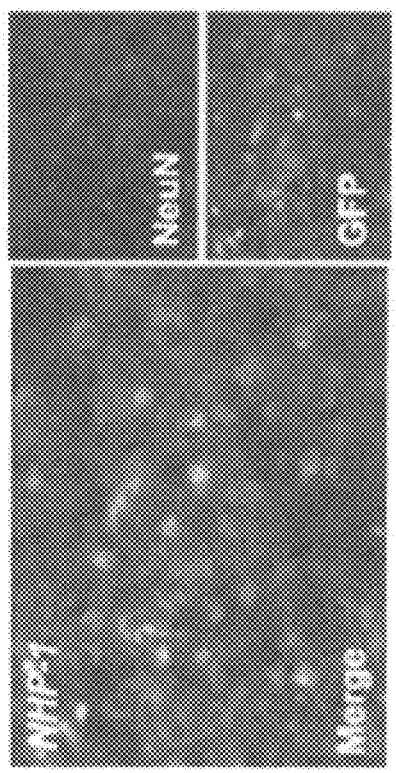
FIGS. 3A through 3F are imaged showing cellular tropism of the AAV9 vectors at the site of infusion in the putamen of the indicated targets (NeuN, GFAP, Iba1 in red), GFP (green) and double-labeled immunofluorescence (yellow).
Figure 3B:
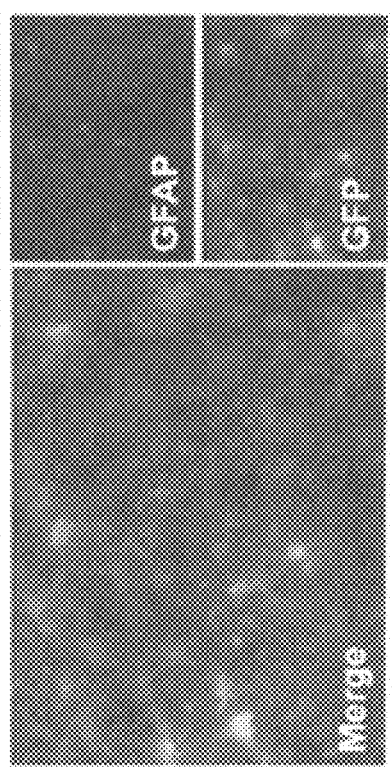
Figure 3C:
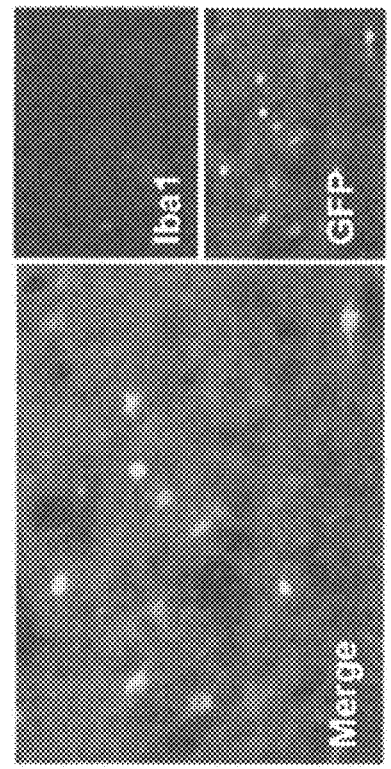
Figure 3D:
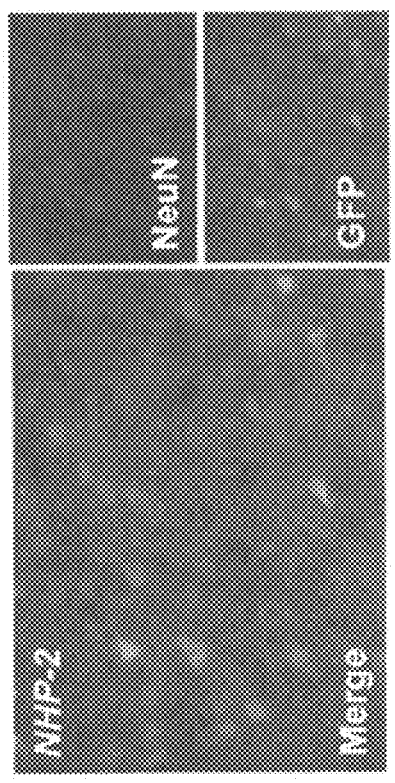
Figure 3E:
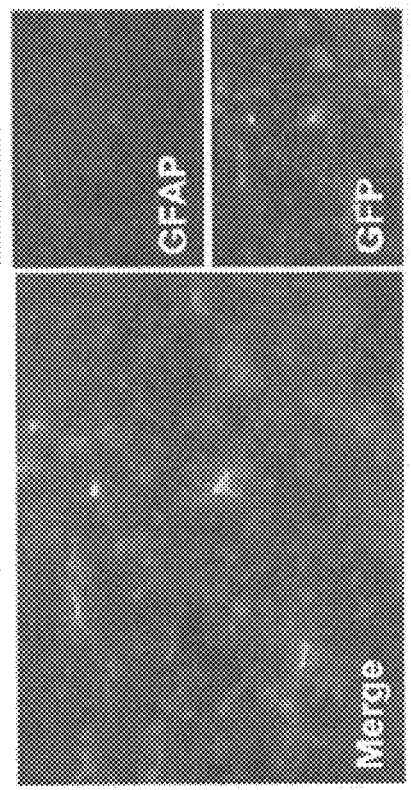
Figure 3F:
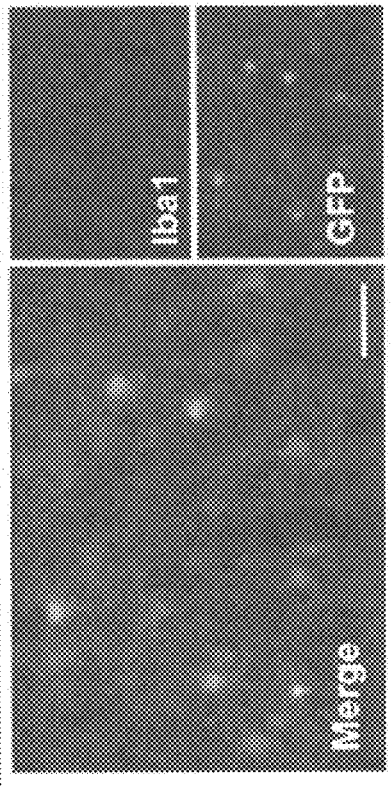

Disclosed herein are compositions and methods for widespread CNS delivery of compositions for detecting, monitoring disease progression, treating and/or preventing Huntington's disease (HD). In particular, the compositions and methods described herein use AAV9 vectors for delivery of Htt repressors, which provides for the spread of functional Htt repressors beyond the site of delivery. The Htt repressors (e.g., Htt-modulating transcription factors, such as Htt-modulating transcription factors comprising zinc finger proteins (ZFP TFs), TALEs (TALE-TF), or CRISPR/Cas-TFs for example, ZFP-TFs, TALE-TFs or CRISPR/Cas-TFs which repress expression of a mutant Htt allele) modify the CNS such that the effects and/or symptoms of HD are reduced or eliminated, for example by reducing the aggregation of Htt in HD neurons, by increasing HD neuron energetics (e.g., increasing ATP levels), by reducing apoptosis in HD neurons and/or by reducing motor deficits in HD subjects.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide," and "protein" are used interchangeably to refer to a polymer of amino acid residues. The term also applies to amino acid polymers in which one or more amino acids are chemical analogues or modified derivatives of a corresponding naturally-occurring amino acid.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Pat. No. 8,586,526.

"TtAgo" is a prokaryotic Argonaute protein thought to be involved in gene silencing. TtAgo is derived from the bacteria *Thermus thermophilus*. See, e.g., Swarts et al. (2014) *Nature* 507(7491):258-261, G. Sheng et al. (2013) *Proc. Natl. Acad. Sci. U.S.A.* 111:652). A "TtAgo system" is all the components required including, for example, guide DNAs for cleavage by a TtAgo enzyme. "Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

Zinc finger binding domains or TALE DNA binding domains can be "engineered" to bind to a predetermined nucleotide sequence, for example via engineering (altering one or more amino acids) of the recognition helix region of a naturally occurring zinc finger protein or by engineering the RVDs of a TALE protein. Therefore, engineered zinc finger proteins or TALEs are proteins that are non-naturally occurring. Non-limiting examples of methods for engineering zinc finger proteins or TALEs are design and selection. A "designed" zinc finger protein or TALE is a protein not occurring in nature whose design/composition results principally from rational criteria. Rational criteria for design include application of substitution rules and computerized algorithms for processing information in a database storing information of existing ZFP designs and binding data. A "selected" zinc finger protein or TALE is a protein not found in nature whose production results primarily from an empirical process such as phage display, interaction trap or hybrid selection. See, for example, U.S. Pat. Nos. 8,586,526; 6,140,081; 6,453,242; 6,746,838; 7,241,573; 6,866,997; 7,241,574 and 6,534,261; see also International Patent Publication No. WO 03/016496.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules.

Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid. The term also includes systems in which a polynucleotide component associates with a polypeptide component to form a functional molecule (e.g., a CRISPR/Cas system in which a single guide RNA associates with a functional domain to modulate gene expression).

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "multimerization domain", (also referred to as a "dimerization domain" or "protein interaction domain") is a domain incorporated at the amino, carboxy or amino and carboxy terminal regions of a ZFP TF or TALE TF. These domains allow for multimerization of multiple ZFP TF or TALE TF units such that larger tracts of trinucleotide repeat domains become preferentially bound by multimerized ZFP TFs or TALE TFs relative to shorter tracts with wild-type numbers of lengths. Examples of multimerization domains include leucine zippers. Multimerization domains may also be regulated by small molecules wherein the multimerization domain assumes a proper conformation to allow for interaction with another multimerization domain only in the presence of a small molecule or external ligand. In this way, exogenous ligands can be used to regulate the activity of these domains.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP or TALE protein as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP or TALE DNA-binding domain is fused to an activation domain, the ZFP or TALE DNA-binding domain and the activation domain are in operative linkage if, in the fusion polypeptide, the ZFP or TALE DNA-binding domain portion is able to bind its target site and/or its binding site, while the activation domain is able to upregulate gene expression. ZFPs fused to domains capable of regulating gene expression are collectively referred to as "ZFP-TFs" or "zinc finger transcription factors", while TALEs fused to domains capable of regulating gene expression are collectively referred to as "TALE-TFs" or "TALE transcription factors." When a fusion polypeptide in which a ZFP DNA-binding domain is fused to a cleavage domain (a "ZFN" or "zinc finger nuclease"), the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site. When a fusion polypeptide in which a TALE DNA-binding domain is fused to a cleavage domain (a "TALEN" or "TALE nuclease"), the TALE DNA-binding domain and the cleavage domain are in operative linkage if, in the fusion polypeptide, the TALE DNA-binding domain portion is able to bind its target site and/or its binding site, while the cleavage domain is able to cleave DNA in the vicinity of the target site. With respect to a fusion polypeptide in which a Cas DNA-binding domain is fused to an activation domain, the Cas DNA-binding domain and the activation domain are in operative linkage if, in the fusion polypeptide, the Cas DNA-binding domain portion is able to bind its target site and/or its binding site, while the activation domain is able to up-regulate gene expression. When a fusion polypeptide in which a Cas DNA-binding domain is fused to a cleavage domain, the Cas DNA-binding domain and the cleavage domain are in operative linkage if, in the fusion polypeptide, the Cas DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and International Patent Publication No. WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

DNA-Binding Domains

The methods described herein make use of compositions, for example Htt-modulating transcription factors, comprising a DNA-binding domain that specifically binds to a target sequence in an Htt gene, particularly that bind to a mutant Htt allele comprising a plurality of trinucleotide repeats.

Any polynucleotide or polypeptide DNA-binding domain can be used in the compositions and methods disclosed herein, for example DNA-binding proteins (e.g., ZFPs or TALEs) or DNA-binding polynucleotides (e.g., single guide RNAs). In certain embodiments, the DNA-binding domain binds to a target site comprising 9 to 28 (or any value therebetween including 10, 11, 12, 13, 14, 15, 16, 17, 18, 19, 20, 21, 22, 23, 24, 25, 26 or 27) contiguous nucleotides of SEQ ID NO:6.

In certain embodiments, the Htt-modulating transcription factor, or DNA binding domain therein, comprises a zinc finger protein. Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; and 6,200,759 and International Patent Publication Nos. WO 95/19431; WO 96/06166; WO 98/53057; WO 98/54311; WO 00/27878; WO 01/60970; WO 01/88197; WO 02/099084; WO 98/53058; WO 98/53059; WO 98/53060; WO 02/016536; and WO 03/016496.

In certain embodiments, the ZFPs can bind selectively to either a mutant Htt allele or a wild-type Htt sequence. Htt target sites typically include at least one zinc finger but can include a plurality of zinc fingers (e.g., 2, 3, 4, 5, 6 or more fingers). Usually, the ZFPs include at least three fingers. Certain of the ZFPs include four, five or six fingers, while some ZFPs include 8, 9, 10, 11 or 12 fingers. The ZFPs that include three fingers typically recognize a target site that includes 9 or 10 nucleotides; ZFPs that include four fingers typically recognize a target site that includes 12 to 14 nucleotides; while ZFPs having six fingers can recognize target sites that include 18 to 21 nucleotides. The ZFPs can also be fusion proteins that include one or more regulatory domains, which domains can be transcriptional activation or repression domains. In some embodiments, the fusion protein comprises two ZFP DNA binding domains linked together. These zinc finger proteins can thus comprise 8, 9, 10, 11, 12 or more fingers. In some embodiments, the two DNA binding domains are linked via an extendable flexible linker such that one DNA binding domain comprises 4, 5, or 6 zinc fingers and the second DNA binding domain comprises an additional 4, 5, or 5 zinc fingers. In some embodiments, the linker is a standard inter-finger linker such that the finger array comprises one DNA binding domain comprising 8, 9, 10, 11 or 12 or more fingers. In other embodiments, the linker is an atypical linker such as a flexible linker. The DNA binding domains are fused to at least one regulatory domain and can be thought of as a 'ZFP-ZFP-TF' architecture. Specific examples of these embodiments can be referred to as "ZFP-ZFP-KOX" which comprises two DNA binding domains linked with a flexible linker and fused to a KOX repressor and "ZFP-KOX-ZFP-KOX" where two ZFP-KOX fusion proteins are fused together via a linker.

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22:1125-1127; Jasin (1996) *Trends Genet.* 12:224-228; Gimble et al. (1996) *J Mol. Biol.* 263:163-180; Argast et al. (1998) *J Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 2007/0117128.

"Two handed" zinc finger proteins are those proteins in which two clusters of zinc finger DNA binding domains are separated by intervening amino acids so that the two zinc finger domains bind to two discontinuous target sites. An example of a two handed type of zinc finger binding protein is SIP1, where a cluster of four zinc fingers is located at the amino terminus of the protein and a cluster of three fingers is located at the carboxyl terminus (see Remade et al. (1999) *EMBO Journal* 18(18):5073-5084). Each cluster of zinc fingers in these proteins is able to bind to a unique target sequence and the spacing between the two target sequences can comprise many nucleotides. Two-handed ZFPs may include a functional domain, for example fused to one or both of the ZFPs. Thus, it will be apparent that the functional domain may be attached to the exterior of one or both ZFPs (see, FIG. 1C) or may be positioned between the ZFPs (attached to both ZFPs) (see, FIG. 4).

Specific examples of Htt-targeted ZFPs are disclosed in U.S. Patent Publication No. 2013/0253040, which is incorporated by reference for all purposes in its entirety herein, as well as in Table 1 below. The first column in this table is an internal reference name (number) for a ZFP and corresponds to the same name in column 1 of Table 2. "F" refers to the finger and the number following "F" refers which zinc finger (e.g., "F1" refers to finger 1).

TABLE 1

Htt-targeted zinc finger proteins

| SBS # | Design | | | | | |
|---|---|---|---|---|---|---|
| | F1 | F2 | F3 | F4 | F5 | F6 |
| 45643 | QSGDLTR (SEQ ID NO: 1) | QSGDLTR (SEQ ID NO: 1) | QSGDLTR (SEQ ID NO: 1) | KHGNLSE (SEQ ID NO: 2) | KRCNLRC (SEQ ID NO: 3) | |
| 46025 | CPSHLTR (SEQ ID NO: 4) | QSGDLTR (SEQ ID NO: 1) | KHGNLSE (SEQ ID NO: 2) | KRCNLRC (SEQ ID NO: 3) | RQFNRHQ (SEQ ID NO: 5) | |

The sequence and location for the target sites of these proteins are disclosed in Table 2. Nucleotides in the target site that are contacted by the ZFP recognition helices are indicated in uppercase letters; non-contacted nucleotides indicated in lowercase.

TABLE 2

Target sites on human and mouse Htt

| SBS # | Target Site |
|---|---|
| 45643 | agCAGCAGcaGCAGCAGCAgcagcagca (SEQ ID NO: 6) |
| 46025 | agCAGCAGCAGcaGCAGCAgcagcagca (SEQ ID NO: 6) |

In certain embodiments, the DNA-binding domain comprises a naturally occurring or engineered (non-naturally occurring) TAL effector (TALE) DNA binding domain. See, e.g., U.S. Pat. No. 8,586,526, incorporated by reference in its entirety herein.

The plant pathogenic bacteria of the genus *Xanthomonas* are known to cause many diseases in important crop plants. Pathogenicity of *Xanthomonas* depends on a conserved type III secretion (T3 S) system which injects more than 25 different effector proteins into the plant cell. Among these injected proteins are transcription activator-like effectors (TALE) which mimic plant transcriptional activators and manipulate the plant transcriptome (see Kay et al. (2007) *Science* 318:648-651). These proteins contain a DNA binding domain and a transcriptional activation domain. One of the most well characterized TALEs is AvrBs3 from *Xanthomonas campestgris* pv. *Vesicatoria* (see Bonas et al. (1989) *Mol Gen Genet* 218:127-136 and International Patent Publication No. WO 2010/079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al. (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al. (2007) *Appl and Envir Micro* 73(13):4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

Specificity of these TALEs depends on the sequences found in the tandem repeats. The repeated sequence comprises approximately 102 bp and the repeats are typically 91-100% homologous with each other (Bonas et al., ibid). Polymorphism of the repeats is usually located at positions 12 and 13 and there appears to be a one-to-one correspondence between the identity of the hypervariable diresidues at positions 12 and 13 with the identity of the contiguous nucleotides in the TALE's target sequence (see Moscou and Bogdanove (2009) *Science* 326:1501 and Boch et al. (2009) *Science* 326:1509-1512). Experimentally, the code for DNA recognition of these TALEs has been determined such that an HD sequence at positions 12 and 13 leads to a binding to cytosine (C), NG binds to T, NI to A, C, G or T, NN binds to A or G, and NG binds to T. These DNA binding repeats have been assembled into proteins with new combinations and numbers of repeats, to make artificial transcription factors that are able to interact with new sequences. In addition, U.S. Pat. No. 8,586,526 and U.S. Patent Publication No. 2013/0196373, incorporated by reference in their entireties herein, describe TALEs with N-cap polypeptides, C-cap polypeptides (e.g., +63, +231 or +278) and/or novel (atypical) RVDs.

Exemplary TALE are described in U.S. Patent Publication No. 2013/0253040, incorporated by reference in its entirety.

In certain embodiments, the DNA binding domains include a dimerization and/or multimerization domain, for example a coiled-coil (CC) and dimerizing zinc finger (DZ). See, U.S. Patent Publication No. 2013/0253040.

In still further embodiments, the DNA-binding domain comprises a single-guide RNA of a CRISPR/Cas system, for example sgRNAs as disclosed in 20150056705.

Compelling evidence has recently emerged for the existence of an RNA-mediated genome defense pathway in archaea and many bacteria that has been hypothesized to parallel the eukaryotic RNAi pathway (for reviews, see Godde and Bickerton (2006) *J. Mol. Evol.* 62:718-729; Lillestol et al. (2006) *Archaea* 2:59-72; Makarova et al. (2006) *Biol. Direct* 1:7; Sorek et al. (2008) *Nat. Rev. Microbiol.* 6:181-186). Known as the CRISPR-Cas system or prokaryotic RNAi (pRNAi), the pathway is proposed to arise from two evolutionarily and often physically linked gene loci: the CRISPR (clustered regularly interspaced short palindromic repeats) locus, which encodes RNA components of the system, and the cas (CRISPR-associated) locus, which encodes proteins (Jansen et al. (2002) *Mol. Microbiol.* 43:1565-1575; Makarova et al. (2002) *Nucleic Acids Res.* 30:482-496; Makarova et al. (2006) *Biol. Direct* 1:7; Haft et al. (2005) *PLoS Comput. Biol.* 1:e60). CRISPR loci in microbial hosts contain a combination of CRISPR-associated (Cas) genes as well as non-coding RNA elements capable of programming the specificity of the CRISPR-mediated nucleic acid cleavage. The individual Cas proteins do not share significant sequence similarity with protein components of the eukaryotic RNAi machinery, but have analogous predicted functions (e.g., RNA binding, nuclease, helicase, etc.) (Makarova et al. (2006) *Biol. Direct* 1:7). The CRISPR-associated (cas) genes are often associated with CRISPR repeat-spacer arrays. More than forty different Cas protein families have been described. Of these protein families, Cas1 appears to be ubiquitous among different CRISPR/Cas systems. Particular combinations of cas genes and repeat structures have been used to define 8 CRISPR subtypes (Ecoli, Ypest, Nmeni, Dvulg, Tneap, Hmari, Apern, and Mtube), some of which are associated with an additional gene module encoding repeat-associated mysterious proteins (RAMPs). More than one CRISPR subtype may occur in a single genome. The sporadic distribution of the CRISPR/Cas subtypes suggests that the system is subject to horizontal gene transfer during microbial evolution.

The Type II CRISPR, initially described in *S. pyogenes*, is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences where processing occurs by a double strand-specific RNase III in the presence of the Cas9 protein. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. In addition, the tracrRNA must also be present as it base pairs with the crRNA at its 3' end, and this association triggers Cas9 activity. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation,' (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system.

Type II CRISPR systems have been found in many different bacteria. BLAST searches on publically available genomes by Fonfara et al. ((2013) *Nuc Acid Res* 42(4):2377-2590) found Cas9 orthologs in 347 species of bacteria. Additionally, this group demonstrated in vitro CRISPR/Cas cleavage of a DNA target using Cas9 orthologs from *S. pyogenes, S. mutans, S. therophilus, C. jejuni, N. meningitides, P. multocida* and *F. novicida*. Thus, the term "Cas9" refers to an RNA guided DNA nuclease comprising a DNA binding domain and two nuclease domains, where the gene encoding the Cas9 may be derived from any suitable bacteria.

The Cas9 protein has at least two nuclease domains: one nuclease domain is similar to a HNH endonuclease, while the other resembles a Ruv endonuclease domain. The HNH-type domain appears to be responsible for cleaving the DNA strand that is complementary to the crRNA while the Ruv domain cleaves the non-complementary strand. The Cas 9 nuclease can be engineered such that only one of the nuclease domains is functional, creating a Cas nickase (see Jinek et al., ibid). Nickases can be generated by specific mutation of amino acids in the catalytic domain of the enzyme, or by truncation of part or all of the domain such that it is no longer functional. Since Cas 9 comprises two nuclease domains, this approach may be taken on either domain. A double strand break can be achieved in the target DNA by the use of two such Cas 9 nickases. The nickases will each cleave one strand of the DNA and the use of two will create a double strand break.

The requirement of the crRNA-tracrRNA complex can be avoided by use of an engineered "single-guide RNA" (sgRNA) that comprises the hairpin normally formed by the annealing of the crRNA and the tracrRNA (see Jinek et al. (2012) *Science* 337:816 and Cong et al. (2013) Sciencexpress/10.1126/science.1231143). In *S. pyogenes*, the engineered tracrRNA:crRNA fusion, or the sgRNA, guides Cas9 to cleave the target DNA when a double strand RNA:DNA heterodimer forms between the Cas associated RNAs and the target DNA. This system comprising the Cas9 protein and an engineered sgRNA containing a PAM sequence has been used for RNA guided genome editing (see Ramalingam ibid) and has been useful for zebrafish embryo genomic editing in vivo (see Hwang et al. (2013) *Nature Biotechnology* 31 (3):227) with editing efficiencies similar to ZFNs and TALENs.

The primary products of the CRISPR loci appear to be short RNAs that contain the invader targeting sequences, and are termed guide RNAs or prokaryotic silencing RNAs (psiRNAs) based on their hypothesized role in the pathway (Makarova et al. (2006) *Biol. Direct* 1:7; Hale et al. (2008) *RNA* 14:2572-2579). RNA analysis indicates that CRISPR locus transcripts are cleaved within the repeat sequences to release ~60- to 70-nt RNA intermediates that contain individual invader targeting sequences and flanking repeat fragments (Tang et al. (2002) *Proc. Natl. Acad. Sci.* 99:7536-7541; Tang et al. (2005) *Mol. Microbiol.* 55:469-481; Lillestol et al. (2006) *Archaea* 2:59-72; Brouns et al. (2008) *Science* 321:960-964; Hale et al. (2008) *RNA* 14:2572-2579). In the archaeon *Pyrococcus furiosus*, these intermediate RNAs are further processed to abundant, stable ~35- to 45-nt mature psiRNAs (Hale et al. (2008) *RNA* 14:2572-2579).

The requirement of the crRNA-tracrRNA complex can be avoided by use of an engineered "single-guide RNA" (sgRNA) that comprises the hairpin normally formed by the annealing of the crRNA and the tracrRNA (see Jinek et al. (2012) *Science* 337:816 and Cong et al. (2013) Sciencexpress/10.1126/science.1231143). In *S. pyrogenes*, the engineered tracrRNA:crRNA fusion, or the sgRNA, guides Cas9 to cleave the target DNA when a double strand RNA:DNA heterodimer forms between the Cas associated RNAs and the target DNA. This system comprising the Cas9 protein and an engineered sgRNA containing a PAM sequence has been used for RNA guided genome editing (see Ramalingam ibid) and has been useful for zebrafish embryo genomic editing in vivo (see Hwang et al. (2013) *Nature Biotechnology* 31(3):227) with editing efficiencies similar to ZFNs and TALENs.

Chimeric or sgRNAs can be engineered to comprise a sequence complementary to any desired target. In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. In some embodiments, the RNAs comprise 22 bases of complementarity to a target and of the form G[n19], followed by a protospacer-adjacent motif (PAM) of the form NGG or NAG for use with a *S. pyogenes* CRISPR/Cas system. Thus, in one method, sgRNAs can be designed by utilization of a known ZFN target in a gene of interest by (i) aligning the recognition sequence of the ZFN heterodimer with the reference sequence of the relevant genome (human, mouse, or of a particular plant species); (ii) identifying the spacer region between the ZFN half-sites; (iii) identifying the location of the motif G[N20]GG that is closest to the spacer region (when more than one such motif overlaps the spacer, the motif that is centered relative to the spacer is chosen); (iv) using that motif as the core of the sgRNA. This method advantageously relies on proven nuclease targets. Alternatively, sgRNAs can be designed to target any region of interest simply by identifying a suitable target sequence the conforms to the G[n20]GG formula. Along with the complementarity region, an sgRNA may comprise additional nucleotides to extend to tail region of the tracrRNA portion of the sgRNA (see Hsu et al. (2013) *Nature Biotech* doi:10.1038/nbt.2647). Tails may be of +67 to +85 nucleotides, or any number therebetween with a preferred length of +85 nucleotides. Truncated sgRNAs may also be used, "tru-gRNAs" (see Fu et al. (2014) *Nature Biotech* 32(3):279). In tru-gRNAs, the complementarity region is diminished to 17 or 18 nucleotides in length.

Further, alternative PAM sequences may also be utilized, where a PAM sequence can be NAG as an alternative to NGG (Hsu 2014, ibid) using a *S. pyogenes* Cas9. Additional PAM sequences may also include those lacking the initial G (Sander and Joung (2014) *Nature Biotech* 32(4):347). In addition to the *S. pyogenes* encoded Cas9 PAM sequences, other PAM sequences can be used that are specific for Cas9 proteins from other bacterial sources. For example, the PAM sequences shown below (adapted from Sander and Joung, ibid, and Esvelt et al. (2013) *Nat Meth* 10(11):1116) are specific for these Cas9 proteins:

| Species | PAM |
| --- | --- |
| S. pyogenes | NGG |
| S. pyogenes | NAG |
| S. mutans | NGG |
| S. thermophilius | NGGNG |
| S. thermophilius | NNAAAW |
| S. thermophilius | NNAGAA |
| S. thermophilius | NNNGATT |
| C. jejuni | NNNNACA |
| N. meningitides | NNNNGATT |
| P. multocida | GNNNCNNA |
| F. novicida | NG |

Thus, a suitable target sequence for use with a S. pyogenes CRISPR/Cas system can be chosen according to the following guideline: [n17, n18, n19, or n20](G/A)G. Alternatively the PAM sequence can follow the guideline G[n17, n18, n19, n20](G/A)G. For Cas9 proteins derived from non-S. pyogenes bacteria, the same guidelines may be used where the alternate PAMs are substituted in for the S. pyogenes PAM sequences.

Most preferred is to choose a target sequence with the highest likelihood of specificity that avoids potential off target sequences. These undesired off target sequences can be identified by considering the following attributes: i) similarity in the target sequence that is followed by a PAM sequence known to function with the Cas9 protein being utilized; ii) a similar target sequence with fewer than three mismatches from the desired target sequence; iii) a similar target sequence as in ii), where the mismatches are all located in the PAM distal region rather than the PAM proximal region (there is some evidence that nucleotides 1-5 immediately adjacent or proximal to the PAM, sometimes referred to as the 'seed' region (Wu et al. (2014) Nature Biotech doi:10.1038/nbt2889) are the most critical for recognition, so putative off target sites with mismatches located in the seed region may be the least likely to be recognized by the sg RNA); and iv) a similar target sequence where the mismatches are not consecutively spaced or are spaced greater than four nucleotides apart (Hsu 2014, ibid). Thus, by performing an analysis of the number of potential off target sites in a genome for whichever CRIPSR/Cas system is being employed, using these criteria above, a suitable target sequence for the sgRNA may be identified.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. In some aspects, a functional derivative may comprise a single biological property of a naturally occurring Cas protein. In other aspects, a function derivative may comprise a subset of biological properties of a naturally occurring Cas protein. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

Exemplary CRISPR/Cas nuclease systems targeted to specific genes are disclosed for example, in U.S. Patent Publication No. 2015/0056705.

Thus, the nuclease comprises a DNA-binding domain in that specifically binds to a target site in any gene into which it is desired to insert a donor (transgene) in combination with a nuclease domain that cleaves DNA.

Fusion Molecules

The DNA-binding domains may be fused to any additional molecules (e.g., polypeptides) for use in the methods described herein. In certain embodiments, the methods employ fusion molecules comprising at least one DNA-binding molecule (e.g., ZFP, TALE or single guide RNA) and a heterologous regulatory (functional) domain (or functional fragment thereof).

In certain embodiments, the functional domain comprises a transcriptional regulatory domain. Common domains include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases) and their associated factors and modifiers. See, e.g., U.S. Patent Publication No. 2013/0253040, incorporated by reference in its entirety herein.

Suitable domains for achieving activation include the HSV VP16 activation domain (see, e.g., Hagmann et al. (1997) J. Virol. 71, 5952-5962) nuclear hormone receptors (see, e.g., Torchia et al. (1998) Curr. Opin. Cell. Biol. 10:373-383); the p65 subunit of nuclear factor kappa B (Bitko & Bank (1998) J Virol. 72:5610-5618 and Doyle & Hunt (1997) Neuroreport 8:2937-2942); Liu et al. (1998) Cancer Gene Ther. 5:3-28), or artificial chimeric functional domains such as VP64 (Beerli et al. (1998) Proc. Natl. Acad. Sci. USA 95:14623-33), and degron (Molinari et al. (1999) EMBO J. 18:6439-6447). Additional exemplary activation domains include, Oct 1, Oct-2A, Sp1, AP-2, and CTF1 (Seipel et al. (1992) EMBO J., 11, 4961-4968 as well as p300, CBP, PCAF, SRC1 PvALF, AtHD2A and ERF-2. See, for example, Robyr et al. (2000) Mol. Endocrinol. 14:329-347; Collingwood et al. (1999) J. Mol. Endocrinol. 23:255-275; Leo et al. (2000) Gene 245:1-11; Manteuffel-Cymborowska (1999) Acta Biochim. Pol. 46:77-89; McKenna et al.

(1999) *J. Steroid Biochem. Mol. Biol.* 69:3-12; Malik et al. (2000) *Trends Biochem. Sci.* 25:277-283; and Lemon et al. (1999) *Curr. Opin. Genet. Dev.* 9:499-504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) *Gene* 245:21-29; Okanami et al. (1996) *Genes Cells* 1:87-99; Goff et al. (1991) *Genes Dev.* 5:298-309; Cho et al. (1999) *Plant Mol. Biol.* 40:419-429; Ulmason et al. (1999) *Proc. Natl. Acad. Sci. USA* 96:5844-5849; Sprenger-Haussels et al. (2000) *Plant J.* 22:1-8; Gong et al. (1999) *Plant Mol. Biol.* 41:33-44; and Hobo et al. (1999) *Proc. Natl. Acad. Sci. USA* 96:15,348-15,353.

Exemplary repression domains include, but are not limited to, KRAB A/B, KOX, TGF-beta-inducible early gene (TIEG), v-erbA, SID, MBD2, MBD3, members of the DNMT family (e.g., DNMT1, DNMT3A, DNMT3B), Rb, and MeCP2. See, for example, Bird et al. (1999) *Cell* 99:451-454; Tyler et al. (1999) *Cell* 99:443-446; Knoepfler et al. (1999) *Cell* 99:447-450; and Robertson et al. (2000) *Nature Genet.* 25:338-342. Additional exemplary repression domains include, but are not limited to, ROM2 and AtHD2A. See, for example, Chem et al. (1996) *Plant Cell* 8:305-321; and Wu et al. (2000) *Plant J.* 22:19-27.

Fusion molecules are constructed by methods of cloning and biochemical conjugation that are well known to those of skill in the art. Fusion molecules comprise a DNA-binding domain and a functional domain (e.g., a transcriptional activation or repression domain). Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion.

Fusions between a polypeptide component of a functional domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, Ill.) Catalogue. Methods and compositions for making fusions between a minor groove binder and a polypeptide have been described. Mapp et al. (2000) *Proc. Natl. Acad. Sci. USA* 97:3930-3935.

The fusion molecule may be formulated with a pharmaceutically acceptable carrier, as is known to those of skill in the art. See, for example, Remington's Pharmaceutical Sciences, 17th ed., 1985; and co-owned International Patent Publication No. WO 00/42219.

The functional component/domain of a fusion molecule can be selected from any of a variety of different components capable of influencing transcription of a gene once the fusion molecule binds to a target sequence via its DNA binding domain. Hence, the functional component can include, but is not limited to, various transcription factor domains, such as activators, repressors, co-activators, co-repressors, and silencers.

In certain embodiments, the fusion protein comprises a DNA-binding domain and a nuclease domain to create functional entities that are able to recognize their intended nucleic acid target through their engineered (ZFP or TALE) DNA binding domains and create nucleases (e.g., zinc finger nuclease or TALE nucleases) cause the DNA to be cut near the DNA binding site via the nuclease activity.

Thus, the methods and compositions described herein are broadly applicable and may involve any nuclease of interest. Non-limiting examples of nucleases include meganucleases, TALENs and zinc finger nucleases. The nuclease may comprise heterologous DNA-binding and cleavage domains (e.g., zinc finger nucleases; TALENs; meganuclease DNA-binding domains with heterologous cleavage domains) or, alternatively, the DNA-binding domain of a naturally-occurring nuclease may be altered to bind to a selected target site (e.g., a meganuclease that has been engineered to bind to site different than the cognate binding site).

The nuclease domain may be derived from any nuclease, for example any endonuclease or exonuclease. Non-limiting examples of suitable nuclease (cleavage) domains that may be fused to Htt DNA-binding domains as described herein include domains from any restriction enzyme, for example a Type IIS Restriction Enzyme (e.g., FokI). In certain embodiments, the cleavage domains are cleavage half-domains that require dimerization for cleavage activity. See, e.g., U.S. Pat. Nos. 8,586,526; 8,409,861; and 7,888,121, incorporated by reference in their entireties herein. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing.

The nuclease domain may also be derived any meganuclease (homing endonuclease) domain with cleavage activity may also be used with the nucleases described herein, including but not limited to I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII.

In certain embodiments, the nuclease comprises a compact TALEN (cTALEN). These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the meganuclease (e.g., TevI) nuclease domain (see Beurdeley et al. (2013) *Nat Comm:* 1-8 DOI: 10.1038/ncomms2782).

In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel et al. (2013) *Nucl Acid Res:* 1-11, doi: 10.1093/nar/gkt1224).

In addition, the nuclease domain of the meganuclease may also exhibit DNA-binding functionality. Any TALENs may be used in combination with additional TALENs (e.g., one or more TALENs (cTALENs or FokI-TALENs) with one or more mega-TALs) and/or ZFNs.

In addition, cleavage domains may include one or more alterations as compared to wild-type, for example for the formation of obligate heterodimers that reduce or eliminate off-target cleavage effects. See, e.g., U.S. Pat. Nos. 7,914,796; 8,034,598; and 8,623,618, incorporated by reference in their entireties herein.

Nucleases as described herein may generate double- or single-stranded breaks in a double-stranded target (e.g., gene). The generation of single-stranded breaks ("nicks") is described, for example in U.S. Pat. No. 8,703,489, incorporated herein by reference which describes how mutation of the catalytic domain of one of the nucleases domains results in a nickase.

Thus, a nuclease (cleavage) domain or cleavage half-domain can be any portion of a protein that retains cleavage activity, or that retains the ability to multimerize (e.g., dimerize) to form a functional cleavage domain.

Alternatively, nucleases may be assembled in vivo at the nucleic acid target site using so-called "split-enzyme" technology (see e.g. U.S. Patent Publication No. 2009/0068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in U.S. Patent Publication No. 2009/0111119. Nuclease expression constructs can be readily designed using methods known in the art.

Expression of the fusion proteins may be under the control of a constitutive promoter or an inducible promoter, for example the galactokinase promoter which is activated (de-repressed) in the presence of raffinose and/or galactose and repressed in presence of glucose. In certain embodiments, the promoter self-regulates expression of the fusion protein, for example via inclusion of high affinity binding sites. See, e.g., U.S. Patent Publication No. 2015/0267205.

Delivery

The proteins and/or polynucleotides (e.g., Htt repressors) and compositions comprising the proteins and/or polynucleotides described herein may be delivered to a target cell by any suitable means including, for example, by injection of proteins, via mRNA and/or using an expression construct (e.g., plasmid, lentiviral vector, AAV vector, Ad vector, etc.). In preferred embodiments, the repressor is delivered using AAV9.

Methods of delivering proteins comprising zinc finger proteins as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 8,586,526; 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more DNA-binding protein-encoding sequences. Thus, when one or more Htt repressors are introduced into the cell, the sequences encoding the protein components and/or polynucleotide components may be carried on the same vector or on different vectors. When multiple vectors are used, each vector may comprise a sequence encoding one or multiple Htt repressors or components thereof.

Conventional viral and non-viral based gene transfer methods can be used to introduce nucleic acids encoding engineered Htt repressors in cells (e.g., mammalian cells) and target tissues. Such methods can also be used to administer nucleic acids encoding such repressors (or components thereof) to cells in vitro. In certain embodiments, nucleic acids encoding the repressors are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson (1992) *Science* 256:808-813; Nabel & Felgner (1993) *TIBTECH* 11:211-217; Mitani & Caskey (1993) *TIBTECH* 11:162-166; Dillon (1993) *TIBTECH* 11:167-175; Miller (1992) *Nature* 357:455-460; Van Brunt (1988) *Biotechnology* 6(10):1149-1154; Vigne (1995) *Restorative Neurology and Neuroscience* 8:35-36; Kremer & Perricaudet (1995) *British Medical Bulletin* 51(1):31-44; Haddada et al. in *Current Topics in Microbiology and Immunology* Doerfler and Böhm (eds.) (1995); and Yu et al. (1994) *Gene Therapy* 1:13-26.

Methods of non-viral delivery of nucleic acids include electroporation, lipofection, microinjection, biolistics, virosomes, liposomes, immunoliposomes, polycation or lipid:nucleic acid conjugates, naked DNA, naked RNA, artificial virions, and agent-enhanced uptake of DNA. Sonoporation using, e.g., the Sonitron 2000 system (Rich-Mar) can also be used for delivery of nucleic acids. In a preferred embodiment, one or more nucleic acids are delivered as mRNA. Also preferred is the use of capped mRNAs to increase translational efficiency and/or mRNA stability. Especially preferred are ARCA (anti-reverse cap analog) caps or variants thereof. See U.S. Pat. Nos. 7,074,596 and 8,153,773, incorporated by reference herein.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™ and Lipofectamine™ RNAiMAX). Cationic and neutral lipids that are suitable for efficient receptor-recognition lipofection of polynucleotides include those of Felgner, International Patent Publication Nos. WO 91/17424 and WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal (1995) *Science* 270:404-410; Blaese et al. (1995) *Cancer Gene Ther.* 2:291-297; Behr et al. (1994) *Bioconjugate Chem.* 5:382-389; Remy et al. (1994) *Bioconjugate Chem.* 5:647-654; Gao et al. (1995) *Gene Therapy* 2:710-722; Ahmad et al. (1992) *Cancer Res.* 52:4817-4820; U.S. Pat. Nos. 4,186,183; 4,217,344; 4,235,871; 4,261,975; 4,485,054; 4,501,728; 4,774,085; 4,837,028; and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al. (2009) *Nature Biotechnology* 27(7):643).

The use of RNA or DNA viral based systems for the delivery of nucleic acids encoding engineered ZFPs, TALEs or CRISPR/Cas systems take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs, TALEs or CRISPR/Cas systems include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon mouse leukemia virus (MuLV), gibbon ape leukemia virus (GaLV), Simian Immunodeficiency virus (SIV), human immunodeficiency virus (HIV), and combinations thereof (see, e.g., Buchscher et al. (1992) *J. Virol.* 66:2731-2739; Johann et al. (1992) *J. Virol.* 66:1635-1640; Sommerfelt et al. (1990) *Virol.* 176: 58-59; Wilson et al. (1989) *J. Virol.* 63:2374-2378; Miller et al. (1991) *J. Virol.* 65:2220-2224; International Patent Publication No. WO 94/26877).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al. (1987) *Virology* 160:38-47; U.S. Pat. No. 4,797,368; International Patent Publication No. WO 93/24641; Kotin (1994) *Human Gene Therapy* 5:793-801; Muzyczka (1994) *J. Clin. Invest.* 94:1351. Construction of recombinant AAV vectors are described in a number of publications, including U.S. Pat. No. 5,173,414; Tratschin et al. (1985) *Mol. Cell. Biol.* 5:3251-3260; Tratschin et al. (1984) *Mol. Cell. Biol.* 4:2072-2081; Hermonat & Muzyczka (1984) *PNAS* 81:6466-6470; and Samulski et al. (1989) *J. Virol.* 63:03822-3828.

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al. (1995) *Blood* 85:3048-305; Kohn et al. (1995) *Nat. Med.* 1:1017-102; Malech et al. (1997) *PNAS* 94(22):12133-12138). PA317/pLASN was the first therapeutic vector used in a gene therapy trial. (Blaese et al. (1995) *Science* 270:475-480). Transduction efficiencies of 50% or greater have been observed for MFG-S packaged vectors. (Ellem et al. (1997) *Immunol Immunother.* 44(1):10-20; Dranoff et al. (1997) *Hum. Gene Ther.* 1:111-2.

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al. (1998) *Lancet* 351(9117): 1702-3, Kearns et al. (1996) *Gene Ther.* 9:748-55). Other AAV serotypes, including AAV1, AAV3, AAV4, AAV5, AAV6, AAV8, AAV 8.2, AAV9, and AAV rh10 and pseudotyped AAV such as AAV2/8, AAV2/5 and AAV2/6 can also be used in accordance with the present invention. In preferred embodiments, AAV9 is used.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al. (1998) *Hum. Gene Ther.* 7:1083-9). Additional examples of the use of adenovirus vectors for gene transfer in clinical trials include Rosenecker et al. (1996) *Infection* 24(1):5-10; Sterman et al. (1998) *Hum. Gene Ther.* 9(7):1083-1089; Welsh et al. (1995) *Hum. Gene Ther.* 2:205-18; Alvarez et al. (1997) *Hum. Gene Ther.* 5:597-613; Topf et al. (1998) *Gene Ther.* 5:507-513; Sterman et al. (1998) *Hum. Gene Ther.* 7:1083-1089.

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al. (1995) *Proc. Natl. Acad. Sci. USA* 92:9747-9751, reported that Moloney mouse leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion, including direct injection into the brain) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

In certain embodiments, the compositions as described herein (e.g., polynucleotides and/or proteins) are delivered directly in vivo. The compositions (cells, polynucleotides and/or proteins) may be administered directly into the central nervous system (CNS), including but not limited to direct injection into the brain or spinal cord. One or more areas of the brain may be targeted, including but not limited to, the hippocampus, the substantia nigra, the nucleus basalis of Meynert (NBM), the striatum and/or the cortex. Alternatively or in addition to CNS delivery, the compositions may be administered systemically (e.g., intravenous, intraperitoneal, intracardial, intramuscular, intrathecal, subdermal, and/or intracranial infusion). Methods and compositions for delivery of compositions as described herein directly to a subject (including directly into the CNS) include but are not limited to direct injection (e.g., stereotactic injection) via needle assemblies. Such methods are described, for example, in U.S. Pat. Nos. 7,837,668; 8,092,429, relating to delivery of compositions (including expression vectors) to the brain and U.S. Patent Publication No. 2006/0239966, incorporated herein by reference in their entireties.

The effective amount to be administered will vary from patient to patient and according to the mode of administration and site of administration. Accordingly, effective amounts are best determined by the physician administering the compositions and appropriate dosages can be determined readily by one of ordinary skill in the art. After allowing sufficient time for integration and expression (typically 4-15 days, for example), analysis of the serum or other tissue levels of the therapeutic polypeptide and comparison to the initial level prior to administration will determine whether the amount being administered is too low, within the right range or too high. Suitable regimes for initial and subsequent administrations are also variable, but are typified by an initial administration followed by subsequent administrations if necessary. Subsequent administrations may be administered at variable intervals, ranging from daily to annually to every several years. In certain embodiments, when using a viral vector such as AAV, the dose administered is between $1\times10^{10}$ and $5\times10^{15}$ vg/ml (or any value therebetween), even more preferably between $1\times10^{11}$ and $1\times10^{14}$ vg/ml (or any value therebetween), even more preferably between $1\times10^{12}$ and $1\times10^{13}$ vg/ml (or any value therebetween).

To deliver ZFPs using adeno-associated viral (AAV) vectors directly to the human brain, a dose range of $1\times10^{10}$-$5\times10^{15}$ (or any value therebetween, including for example between $1\times10^{11}$ and $1\times10^{14}$ vg/ml or $1\times10^{12}$ and $1\times10^{13}$ vg/ml) vector genome per striatum can be applied. As noted, dosages may be varied for other brain structures and for different delivery protocols. Methods of delivering AAV vectors directly to the brain are known in the art. See, e.g., U.S. Pat. Nos. 9,089,667; 9,050,299; 8,337,458; 8,309,355; 7,182,944; 6,953,575; and 6,309,634.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with at least one Htt repressor or component thereof and re-infused back into the subject organism (e.g., patient). In a preferred embodiment, one or more nucleic acids of the Htt repressor are delivered using AAV9. In other embodiments, one or more nucleic acids of the Htt repressor are delivered as mRNA. Also preferred is the use of capped mRNAs to increase translational efficiency and/or mRNA stability. Especially preferred are ARCA (anti-reverse cap analog) caps or variants thereof. See U.S. Pat. Nos. 7,074,596 and 8,153,773, incorporated by reference herein in their entireties. Various cell types suitable for ex vivo transfection are well known to those of skill in the art (see, e.g., Freshney et al. *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al. (1992) *J. Exp. Med.* 176:1693-1702).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Tad (differentiated antigen presenting cells) (see Inaba et al. (1992) *J. Exp. Med.* 176:1693-1702).

Stem cells that have been modified may also be used in some embodiments. For example, neuronal stem cells that have been made resistant to apoptosis may be used as therapeutic compositions where the stem cells also contain the ZFP TFs of the invention. Resistance to apoptosis may come about, for example, by knocking out BAX and/or BAK using BAX- or BAK-specific TALENs or ZFNs (see, U.S. Pat. No. 8,597,912) in the stem cells, or those that are disrupted in a caspase, again using caspase-6 specific ZFNs for example. These cells can be transfected with the ZFP TFs or TALE TFs that are known to regulate mutant or wild-type Htt.

Vectors (e.g., retroviruses, adenoviruses, liposomes, etc.) containing therapeutic ZFP nucleic acids can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34+ cells, include adenovirus Type 35.

Vectors suitable for introduction of transgenes into immune cells (e.g., T-cells) include non-integrating lentivirus vectors. See, for example, Naldini et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

As noted above, the disclosed methods and compositions can be used in any type of cell including, but not limited to, prokaryotic cells, fungal cells, Archaeal cells, plant cells, insect cells, animal cells, vertebrate cells, mammalian cells and human cells. Suitable cell lines for protein expression are known to those of skill in the art and include, but are not limited to COS, CHO (e.g., CHO-S, CHO-K1, CHO-DG44, CHO-DUXB11), VERO, MDCK, WI38, V79, B14AF28-G3, BHK, HaK, NSO, 5P2/0-Ag14, HeLa, HEK293 (e.g., HEK293-F, HEK293-H, HEK293-T), perC6, insect cells such as *Spodoptera fugiperda* (Sf), and fungal cells such as *Saccharomyces, Pischia* and *Schizosaccharomyces.* Progeny, variants and derivatives of these cell lines can also be used. In a preferred embodiment, the methods and composition are delivered directly to a brain cell, for example in the striatum.

Applications

Htt-binding molecules (e.g., ZFPs, TALEs, CRISPR/Cas systems, Ttago, etc.) as described herein, and the nucleic acids encoding them, can be used for a variety of applications. These applications include therapeutic methods in which a Htt-binding molecule (including a nucleic acid encoding a DNA-binding protein) is administered to a subject (e.g., an AAV such as AAV9) and used to modulate the expression of a target gene within the subject. The modulation can be in the form of repression, for example, repression of mHtt that is contributing to an HD disease state. Alternatively, the modulation can be in the form of activation when activation of expression or increased expression of an endogenous cellular gene can ameliorate a diseased state. In still further embodiments, the modulation can be cleavage (e.g., by one or more nucleases), for example, for inactivation of a mutant Htt gene. As noted above, for such applications, the Htt-binding molecules, or more typically, nucleic acids encoding them are formulated with a pharmaceutically acceptable carrier as a pharmaceutical composition.

The Htt-binding molecules, or vectors encoding them, alone or in combination with other suitable components (e.g. liposomes, nanoparticles or other components known in the art), can be made into aerosol formulations (i.e., they can be "nebulized") to be administered via inhalation. Aerosol formulations can be placed into pressurized acceptable propellants, such as dichlorodifluoromethane, propane, nitrogen, and the like. Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Compositions can be administered, for example, by intravenous infusion, orally, topically, intraperitoneally, intravesically, intracranially or intrathecally. The formulations of compounds can be presented in unit-dose or multi-dose sealed containers, such as ampules and vials. Injection solutions and suspensions can be prepared from sterile powders, granules, and tablets of the kind previously described.

The dose administered to a patient should be sufficient to effect a beneficial therapeutic response in the patient over time. The dose is determined by the efficacy and $K_d$ of the particular Htt-binding molecule employed, the target cell, and the condition of the patient, as well as the body weight or surface area of the patient to be treated. The size of the dose also is determined by the existence, nature, and extent of any adverse side-effects that accompany the administration of a particular compound or vector in a particular patient.

Beneficial therapeutic response can be measured in a number of ways. For example, improvement in Huntington's associates movement disorders such as involuntary jerking or writhing movements, muscle problems, such as rigidity or muscle contracture (dystonia), slow or abnormal eye movements, impaired gait, posture and balance, difficulty with the physical production of speech or swallowing and the impairment of voluntary movements can be measured. Other impairments, such as cognitive and psychiatric disorders can also be monitored for signs of improvement associated with treatment. The UHDRS scale can be used to quantitate clinical features of the disease.

For patients that are pre-symptomatic, treatment can be especially important because it affords the opportunity to treat the disease prior to the extensive neurodegeneration that occurs in HD. This damage initiates prior to the development of the overt symptoms described above. HD pathology primarily involves the toxic effect of mutant Htt in striatal medium spiny neurons. These medium spiny neurons express high levels of phosphodiesterase 10A (PDE10A) which regulates cAMP and cGMP signaling cascades that are involved in gene transcription factors, neurotransmitter receptors and voltage-gated channels (Niccolini et al. (2015) *Brain* 138:3016-3029), and it has been shown that the expression of PDE10A is reduced in HD mice and post-mortem studies in humans found the same. Recently, positron emission tomography (PET) ligands have been developed that are ligands for the PDE10A enzyme (e.g. $^{11}$C-IMA107, (Niccolini et al., ibid; $^{18}$FMNI-659 (Russell et al. (2014) *JAMA Neurol* 71(12):1520-1528), and these molecules have been used to evaluate pre-symptomatic HD patients. The studies have been shown that PDE10A levels are altered in HD patients even before symptoms develop. Thus, evaluation of PDE10A levels by PET can be done before, during and after treatment to measure therapeutic efficacy of the compositions of the invention. "Therapeutic efficacy" can mean improvement of clinical and molecular measurements, and can also mean protecting the patient from any further decreases in medium spiny neuron function or an increase in spiny neuron loss, or from further development of the overt clinical presentations associated with HD.

The following Examples relate to exemplary embodiments of the present disclosure in which the Htt-modulator comprises a zinc finger protein. It will be appreciated that this is for purposes of exemplification only and that other Htt-modulators (e.g., repressors) can be used, including, but not limited to, TALE-TFs, a CRISPR/Cas system, additional ZFPs, ZFNs, TALENs, additional CRISPR/Cas systems (e.g., Cfp systems), homing endonucleases (meganucleases) with engineered DNA-binding domains.

EXAMPLES

Example 1: Htt Repressors

Zinc finger proteins 45643 and 46025 (see Table 1) targeted to Htt were engineered essentially as described in U.S. Pat. No. 6,534,261; U.S. Patent Publication Nos. 2015/0056705; 2011/0082093; 2013/0253040; and 2015/0335708. Table 1 shows the recognition helices of the DNA binding domain of these ZFPs, while Table 2 shows the target sequences of these ZFPs. The ZFPs were evaluated and shown to be bind to their target sites.

ZFPs 45643 and 46025 were operably linked to a KRAB repression domain to form ZFP-TF that repress Htt. The ZFP TFs were transfected into human cells (e.g., cells derived from HD patients) and expression of Htt was monitored using real-time RT-PCR. Both ZFP-TFs were found to be effective in selectively repressing mutant Htt expression. ZFP-TFs are functional repressors when formulated as plasmids, in mRNA form, in Ad vectors, lentiviral vectors and/or in AAV vectors (e.g., AAV9).

Example 2: Materials and Methods

Animals.

Two rhesus monkeys (*Macaca mulatta*, 4-15 years of age, >4 kg) were included in this study. Experiments were performed according to National Institutes of Health guidelines and to protocols approved by the Institutional Animal Care and Use Committee at University of California San Francisco.

Vector Preparation.

AAV9-containing green fluorescent protein (GFP) under the control of the cytomegalovirus promoter was generated by triple transfection of HEK-293 cells as previously described in Matsushita et al. (1998) *Gene Ther* 5:938-945. AAV9-GFP was diluted immediately before use to a concentration of $1.4 \times 10^{13}$ vg/ml (high dose) or $1.4 \times 10^{12}$ vg/ml (low dose) in phosphate-buffered saline and 0.001% (vol/vol) Pluronic F-68.

Surgery and Vector Infusion.

Each NHP underwent stereotactic placement of skull-mounted, MR-compatible temporary plastic plugs. The animal was then placed supine in an MM-compatible stereotactic frame. After craniectomy, the cannula-guides were secured to the skull over both hemispheres. After placement of the plugs, the intubated animal was moved to the platform table in the MM suite and placed on inhaled isoflurane (1-3%). Guides under sterile conditions were filled with MR-visible tracer (Prohance, Singem, Germany) to localize the plugs in the MR images to calculate the trajectory to the target structures inside the brain. Then, the NHP was moved into the MR magnet and high-resolution anatomical MR scan was acquired for target identification and surgical planning. After the target was selected, a custom-designed, ceramic, fused silica reflux-resistant cannula with a 3-mm stepped tip was used for vector infusion as described previously in Richardson et al. (2011) *Mol Ther* 19:1048-1057; Krauze et al. (2005) *J Neurosurg* 103:923-929; and Fiandaca et al. (2008). *Neurotherapeutics* 5:123-127.

The cannula was attached to a 1-ml syringe mounted onto an MRI-compatible infusion pump (Harvard Apparatus, Boston, Mass.). The infusion initiated at 1 μl/min, and after visualizing the infusate at the cannula tip, the cannula was introduced through the guide-stem into the brain. When the depth-stop encountered the top of the guide-stem, it was secured with a locking screw. The infusion rate was ramped up from an initial 1 μl/min to a final 5 μl/min. Each NHP received infusions covering the pre- and post-commissural putamen simultaneously in each putamen (bilateral). The total infusion volume per hemisphere was 100 μl in both hemispheres. Once the infusion ended, guide-devices were removed from the skull, and animals were returned to their home cages and monitored during recovery from anesthesia.

MRI Acquisition.

Animals were scanned on a Siemens Verio Magnetom 3.0T MRI (Siemens, Malvern, Pa.). T1-weighted fast low angle shot (FLASH) acquisitions obtained with a 4° flip angle on the first scan produced a proton-density weighted image to trace gadolinium at the cannula tip (8 ms TE, 28 ms TR, 3 excitations, 256×3×192 matrix, 14×14 mm field of view, 1 mm slices). All subsequent scans were serially acquired at a 40° flip angle to increase the T1-weighting and highlight the Gd signal enhancement.

Tissue Processing.

Animals infused with AAV9 were perfused transcardially approximately 3 weeks after AAV-GFP infusion with cold saline followed by 4% paraformaldehyde. Brains were harvested and histologically analyzed using previously established methods. In short, 6 mm coronal blocks were collected via a brain matrix and immediately post-fixed in paraformaldehyde overnight, then cryoprotected in 30% (w/v) sucrose the following day. A sliding microtome was used to cut 40-μm serial sections. Chromagenic staining was performed on free-floating sections to visualize GFP expression by methods we have previously established.

Immunohistochemistry.

For each serotype, sections were collected in sequence, stored in 100-well containers in cryoprotectant solution (0.5 M sodium phosphate buffer, pH 7.4, 30% glycerol, and 30% ethylene glycol) at 4° C. until further processing. Immunohistochemistry was performed on free-floating sections. Briefly, washes with PBS for the horseradish peroxidase (HRP)-based procedure, or in PBS with 0.1% Tween 20 (PBST) for fluorescence staining, were performed between each immunohistochemical step. Endogenous peroxidase activity (for peroxidase-based procedures) was quenched for 30 minutes at room temperature. Blocking of non-specific staining was accomplished by incubation of sections in 20% horse serum in PBST for 60 min at room temperature. Thereafter, sections were incubated overnight with specific primary antibodies. Primary antibodies used in the immunohistochemical procedures were as follows: polyclonal rabbit anti-Iba1, PAb, 1:500 (www.biocare.net/); monoclonal mouse and anti-GFAP, 1:10,000 for HRP-based staining and polyclonal rabbit anti-GFAP 1:1000 for fluorescence (www.millipore.com); monoclonal mouse anti-NeuN, 1:5,000 for HRP-based staining and 1:500 for fluorescence staining (Millipore); monoclonal and mouse anti-TH, 1:1000 (Millipore, MAB318); polyclonal mouse and monoclonal rabbit anti-GFP, 1:200 and 1:500, respectively, (Life Technologies; Millipore). All antibodies were dissolved in Da Vinci diluent (Biocare). After three rinses in PBS for 5 min at room temperature, sections for HRP-based staining were incubated with either Mach 2 anti-mouse HRP polymer (Biocare) or March 2 anti-rabbit HRP polymer (Biocare) for 1 h at room temperature. The activity of bound HRP was visualized by means of a commercially available kit with 3,3'-diaminobenzidine peroxide substrate (Vectro Labs). NeuN-stained sections were counterstained with Cresyl Violet stain. Finally, immunostained sections were mounted on gelatinized slides, dehydrated in alcohol and xylene and cover-slipped with Cytoseal™ (Fisher Scientific).

For dual fluorescent immunostaining of different antigens (GFP/GFAP, GFP/NeuN, GFP/TH, and GFP/Iba1), a combination of primary antibodies was applied to sections as a cocktail of primary antibodies by overnight incubation at 4° C. All primary antibodies were dissolved in DaVinci diliuent (Biocare). After three washes in PBST, monoclonal primary antibodies were visualized by incubation in the dark for 2 hours with appropriate secondary fluorochrome-conjugated antibodies: goat anti-mouse DyLight 549 (red) (Biocare), goat anti-rabbit DyLight 549, donkey anti-rabbit Alexa Fluor 555 (Life Technologies), goat anti-mouse DyLight 488 (green), goat anti-rabbit DyLight 488, and donkey anti-rabbit Alexa Fluor 488. All secondary antibodies were dissolved at 1:1,000 dilution in Fluorescence Antibody Diluent (Biocare). Sections were cover-slipped with Vectashield Hard Set, Mounting Medium for Fluorescence (Vector Labs). Control sections were processed without primary antibodies, and no significant immunostaining was observed under these conditions.

Semi-Quantitative Analyses.

Distribution volume (Vd) analysis was performed with Brainlab iPlan Flow Suite (Brainlab, Munich, Germany; www.brainlab.com). Infusion sites, cannula tracts and cannula tip were identified on T1-weighted MR images in the coronal, axial, and sagittal planes. Regions of interest (ROIs) were delineated to outline T1 gadolinium signal and target putamen. Three-dimensional volumetric reconstructions of the image series and ROI were analyzed to determine estimated Vd of infusions and its ratio with respect to the total volume of infusate (Vi).

Analysis of Brain Sections.

All processed sections were examined and digitally photographed on a Zeiss Axioskop microscope (Zeiss) equipped with CCD color video camera and image analysis system (Axiovision Software; Zeiss). For each monkey, the number of GFP-positive and NeuN-positive cells was determined in both hemispheres from coronal sections through the putamen. Fluorescence microscopy was used to determine the number of double-labeled cells in sections. Photomicrographs for double-labeled sections were obtained by merging images from two separate channels (red-rhodamine and green-fluorescein isothiocyanate; co-localization appears yellow) without altering the position of the sections or focus (objective×20 and ×40, Carl Zeiss microscopy with Apo-Tome mode). For each double staining, sections were selected anterior and posterior at ~500-μm distance from the site of injection. To identify the proportion of cells expressing GFP/NeuN, GFP/GFAP, GFP/TH and GFP/Iba1, each section was analyzed by first using one channel for the presence of phenotype-specific cells (TH, GFAP, Iba1, or NeuN) and second a combined channel for the number of co-stained cells.

Sections stained for NeuN and GFP were used for counting from three sections at three different levels of the injection site in the putamen (bilateral). NeuN positive and GFP positive cells were counted at 200-fold magnification from 5 randomly acquired frames (350 μm$^2$) in both the transduced area. In the non-transduced area, 5 randomized frames were taken at a distance of 350 μm from the defined border of expression. These analyses permitted quantitative comparisons of the vectors, although they do not reflect the total number of transduced cells in vivo. Cell counts in each sampled region were averaged across sections for each animal and the final data are presented as the mean number of NeuN positive and GFP positive.

Example 3: Infusion and Transduction Efficiency

We have shown previously that AAV2 is a neurotropic vector that is transported in an anterograde direction along neurons when it is infused into the parenchyma of rat and non-human primate (NHP) brain. See, e.g., Ciesielska et al. (2011) *Mol Ther* 19:922-927; Kells et al. (2012) *Neurobiol Dis* 48:228-235. This transport of intact viral particles is sufficiently robust that vector is apparently released from projecting nerve terminals where it is able to transduce distal neurons. Thus, infusion of AAV2 into NHP thalamus resulted in robust transduction of cortical neurons contained entirely within the cortex. In contrast, AAV6 is transported along axons in a retrograde direction and is almost as neurotropic as is AAV2. See, e.g., Salegio et al. (2013) *Gene Ther.* 20(3):348-52; San Sebastian et al. (2013) *Gene Ther* 20:1178-1183. For example, transduction of NHP putamen results in transgene expression of cortico-striatal neurons.

In this study, 2 NHPs received putaminal infusions of AAV9-GFP at either a high dose (HD; left hemisphere; 1.5×10$^{13}$ vg/mL) or a low dose (LD; right hemisphere; 1.5×10$^{12}$ vg/mL). The post-surgical in-life phase was intentionally kept short (3 weeks) in order to limit potential confounds arising from cell-mediated responses to GFP as previously described in Ciesielska et al. (2013) *Mol Ther* 21:158-166; Samaranch et al. (2014) *Mol Ther* 22:329-337.

The distribution of gadolinium-enhanced signal on MRI was evaluated volumetrically as previously described in Richardson et al. (2011) *Stereotact Funct Neurosurg* 89:141-151. Results are shown in FIG. 1. It should be noted that the approximate shape of the primate putamen is somewhat conical in sagittal orientation with the broader cross-section at the anterior end narrowing towards the posterior portion. Coverage of the putamen by MRI contrast reagent was, however, almost complete. The overlap between GFP and gadolinium signal indicated that the infusate was well-contained with little leakage in the anterior and medial portions of the putamen, and expanded over an area threefold that of the MR image contrast area. Immunohistochemical staining for GFP expression was outlined and superimposed against an outline of putamen reconstructed from the baseline sequence of MR images at various coronal levels within the spatial bounds of the infusion. This is quite different from what has been seen with AAV2 where expression of transgene correlated almost exactly with the MRI signal (Fiandaca et al. (2009) *Neuroimage* 47 Suppl 2:T27-35).

Furthermore, robust reporter expression was evident both in HD and in LD putamina with an abundance of cell bodies and neuronal fibers (FIGS. 2A through 2D). We counted GFP+/NeuN+ neurons by immunofluorescence throughout the primary area of transduction (PAT; mm$^2$) in the plane of the cannula tract, based on previously described methods (Ciesielska et al. (2013) Mol Ther 21:158-166). The intensity of GFP-positive neuronal expression diminished promptly along a distinct perimeter ≤350 μm from transduced areas, hereafter described as "outside" the PAT (oPAT). In this part of the study, we performed counted NeuN+ cell bodies in the PAT and oPAT, as well as in putaminal sections processed from two healthy, naïve monkeys in order to ascertain vector-dependent effects.

We further analyzed whether efficiency of transduction at the PAT and oPAT was dependent upon dose in terms of NeuN-positive and GFP-positive labels that appear to reveal AAV9-mediated transduction and GFP expression in neuronal cell bodies. We saw no evidence of any neuronal loss due to AAV9-GFP transduction, consistent with our previous observations of a relatively slow build-up of anti-GFP responses evident more than 6 weeks after AAV9-GFP infusion but not at 3 weeks, although we saw evidence of activation of microglia and MHC-II upregulation (FIGS. 2E through 2H).

There are a number of mechanisms for antigen-presentation in the brain, chiefly astrocytes (Cornet et al. (2000) J Neuroimmunol 106:69-77 and microglia (Nelson et al. (2002) Ann Med 34:491-500). To determine the cellular specificity of AAV9 for neuronal and glial targets at the infusion site, we immunostained brain sections for the transgene and cell-specific markers, including NeuN neuronal marker for neurons, glial fibrillary acid protein (GFAP) for astrocytes, and Iba1, a microglia-specific marker.

As shown in FIG. 3, double immunofluorescence staining against GFP with each of the cellular markers revealed transgene was readily expressed in both neurons and astrocytes, whereas microglia were not transduced despite massive GFP expression in neighboring cell bodies and neuronal fibers. Nevertheless, activation of microglia in transduced regions was readily observable (FIGS. 2E through 2H), indicative of the ability of microglia to sense the innate immune status of their local environment.

Example 4: Axonal Transport

Figures 4A, 4B:
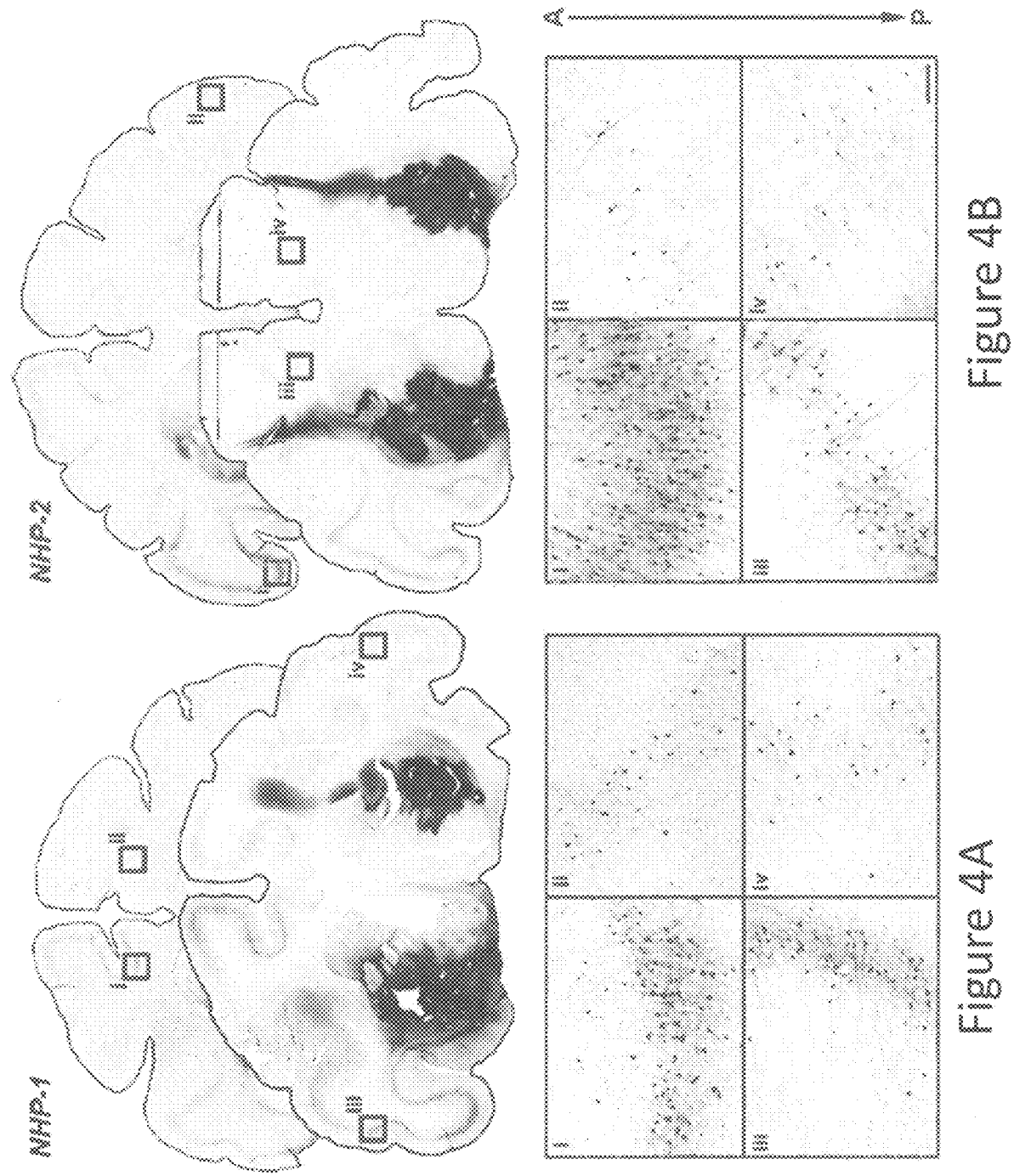
FIGS. 4A and 4B shows retrograde axonal transport of AAV9 from putamen to cortex. Coronal brain sections processed from NHP-1 (FIG. 4A) and NHP-2 (FIG. 4B) anterior (i and ii) and posterior (iii and iv) to the cannula tract showed robust axonal transport of AAV9-GFP along cortico-striatal projections. High magnification images of the areas within the black squared labeled "i" "ii" "iii" and "iv." show increased GFP expression in cortical cell bodies and fibers within the hemisphere receiving high-dose vector indicating a dose effect with respect to the contralateral side. Scale bars: 200 µm.
Figures 5A, 5B:
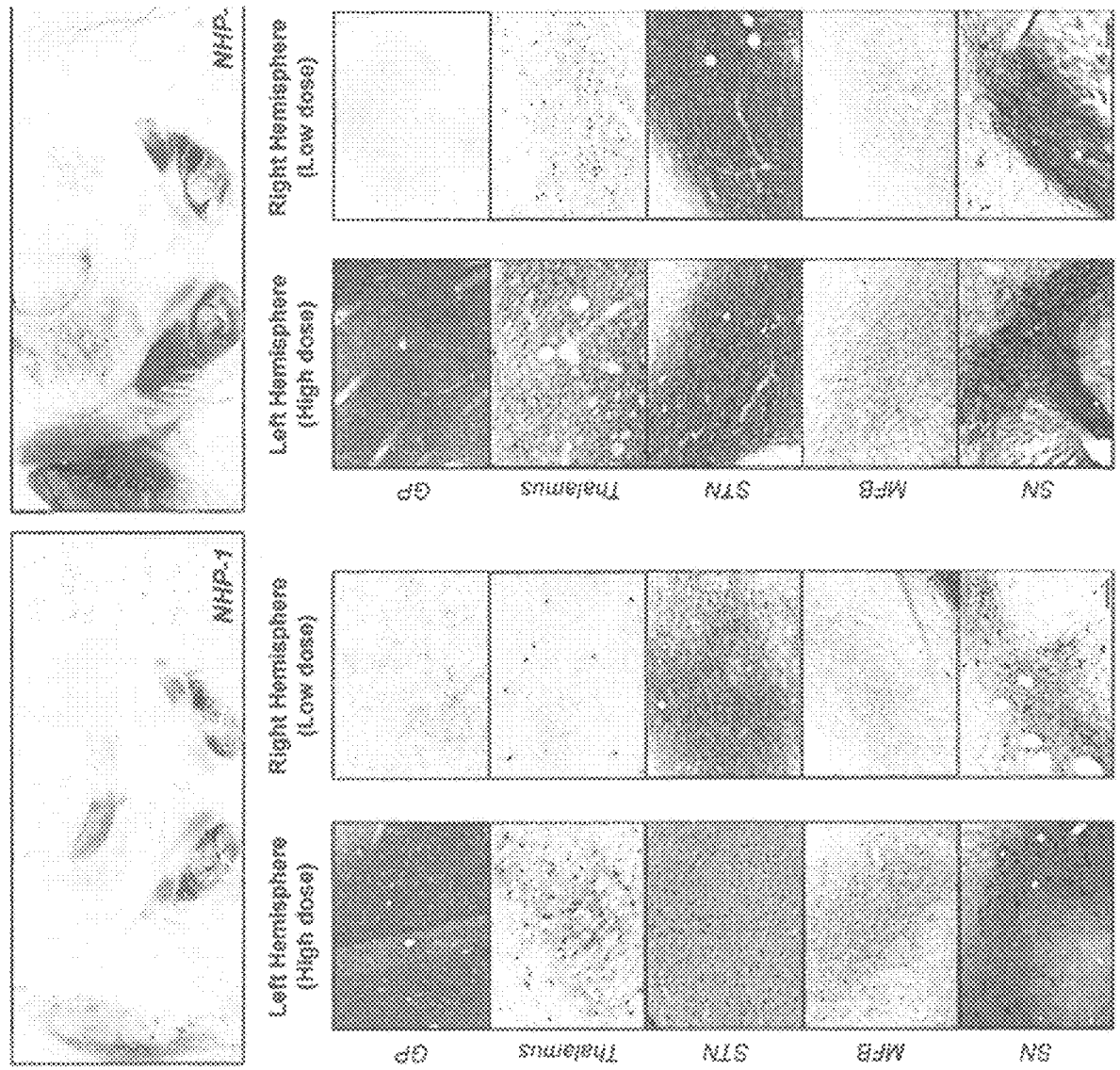
FIGS. 5A and 5B depict axonal transport to distal regions.
Figure 6A:
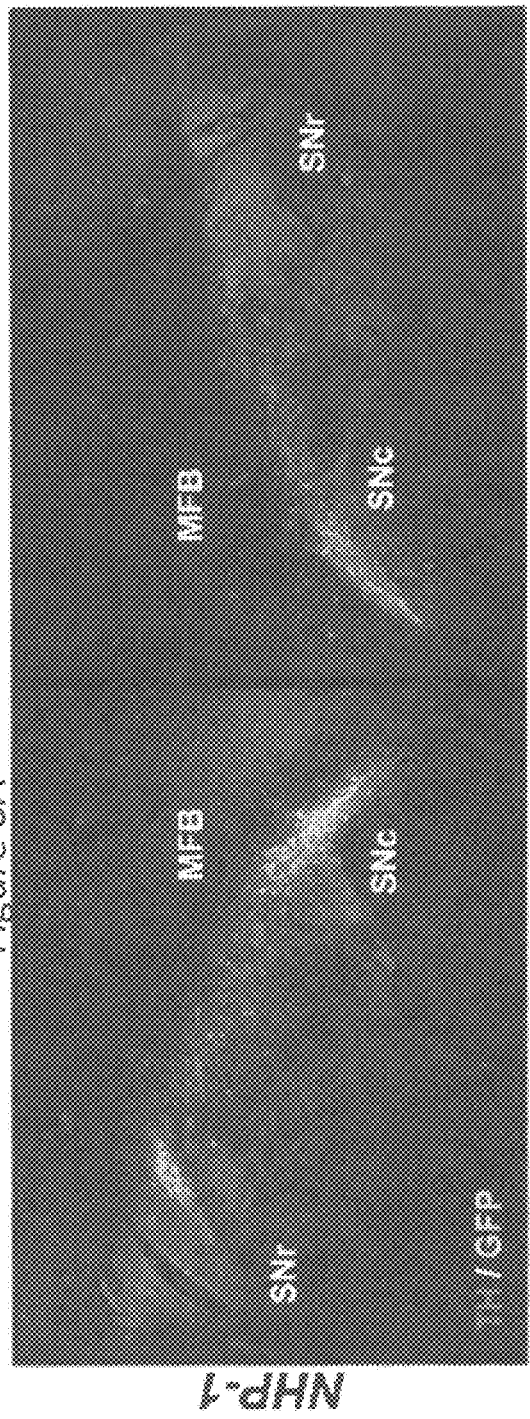
FIGS. 6A and 6B depict axonal transport of AAV to substantia nigra pars reticulata and pars compacta.
Figure 6B:
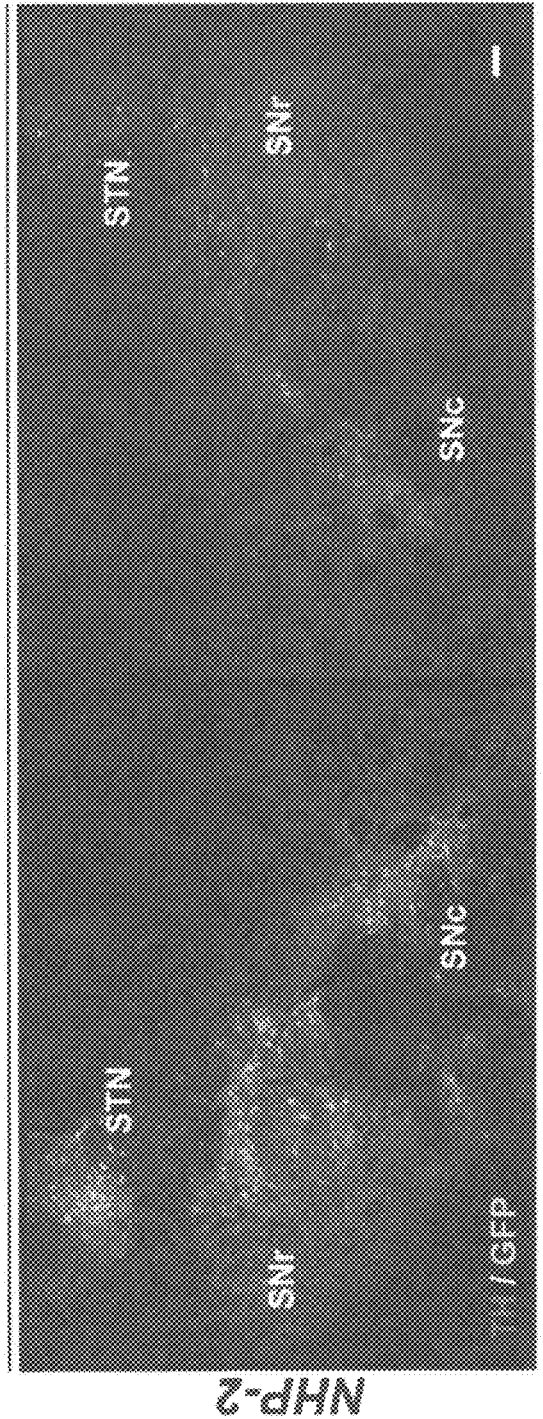
Figure 7:
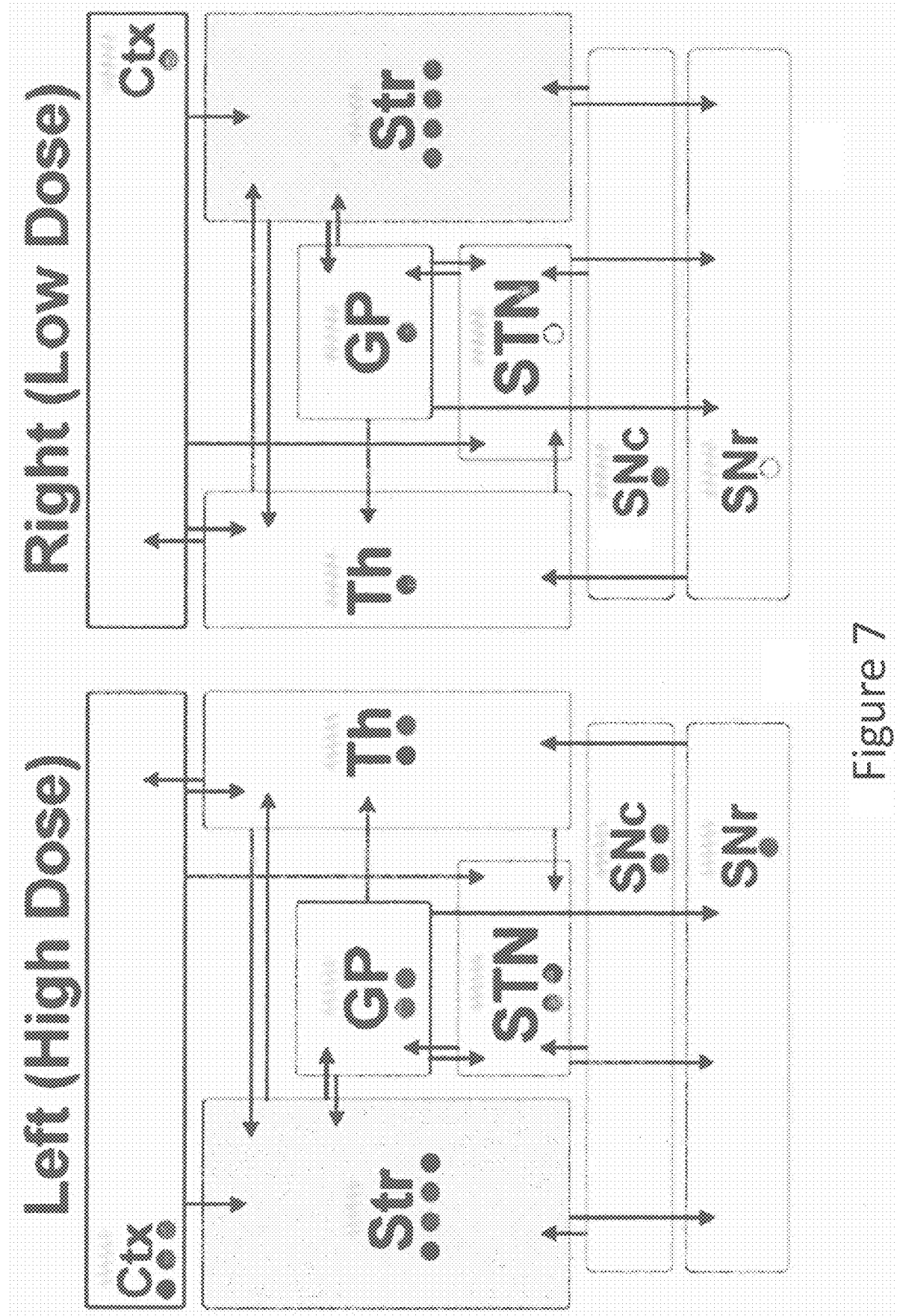
FIG. 7 is a schematic depicting neuronal connection pathways in primate brain. Illustrated anterograde and retrograde transport system and dose effect between high dose (left) and low dose (right) NHP brain hemispheres. AAV9-GFP viral particles at the striatal injection site ("Str"), shaded in grey, were transported retrogradely to secondary brain areas including cortex ("Ctx"), thalamus ("Th") and substantia nigra parts compacta ("SNc"). Anterograde transport of viral particles targeted parts reticulata ("SNr"). Transport either by perivascular spread or anterograde axonal means to the globus pallidus ("GP") led in turn to axonal transport to the subthalamic nucleus ("STN"). The presence of neuronal GFP-positive fibers is indicated by the grey strokes and GFP-positive cells bodies by the black dots. Absence of transduced cell bodies is indicated by empty circles.

Infusion of AAV9-GFP into putamen yielded transduction in distal structures. GFP staining was observed, for example, in cell bodies of the prefrontal, frontal, and parietal cortex (FIG. 4). GFP-positive cell bodies and fibers were also present in thalamus and components of the basal ganglia, including the substantia nigra pars compacta (SNc) and pars reticulata (SNr), as well as subthalamic nucleus (STN) and in fibers of the medial forebrain bundle (MFB) (FIG. 5). There was a strong vector dose-dependence of axonal transport to distal loci (FIG. 7). Thus, the high but not low dose of AAV9 resulted in cell body labeling in STN despite the fact that there is no direct neuronal connection between the putamen and STN. We have previously noted such indirect anterograde transport within basal ganglia with AAV2 (Ciesielska et al. (2011) Mol Ther 19:922-927, and Kells (2012), ibid and from thalamus to cortex (Kells et al. (2009) Proc Natl Acad Sci USA 106:2407-2411). However, the significant dose-dependence of AAV9-GFP transport implies a 2-stage transport of vector first to the globus pallidus and then to STN. Anterograde transport of AAV9 was further supported by the presence of GFP-positive cell bodies within the substantia nigra pars reticulata (SNr) with the presence of fibers marking neurons projecting into SNr from putamen (FIG. 6). Surprisingly, cell bodies in substantia nigra pars compacta (SNc) were also GFP-positive, indicative of retrograde transport from putamen to which SNc sends highly arborized projections. Although not as dramatic a difference as with STN, there was a clear dose effect of AAV9-GFP on transduction in these areas.

Thus, we conclude that AAV9 is transported along axons in both directions, a phenomenon that accounts at least partly for the remarkable distribution of AAV9 in the primate brain. AAV9 differed strikingly from AAV2 and AAV6 in terms of axonal transport and cell-type specificity. AAV9 transduced astrocytes and neurons but not microglia. The vector was transported axonally in both anterograde and retrograde directions. These data advance our understanding of AAV9 distribution in the primate brain and provides support for its use in the treatment of neurological disease with a substantial cortico-striatal pathology such as Huntington's disease.

As clinical development of neurological gene therapy with vectors based on adeno-associated virus (AAV) becomes more common, the behavior of specific serotypes of AAV in the primate brain is becoming more important. This is particularly true in the context of more efficient and advanced vector infusion technologies that are driving clinical development of neurosurgical interventions in diseases such as Parkinson's disease (Richardson et al. (2011) Mol Ther 19:1048-1057) and rare neurological disorders such as aromatic L-amino acid decarboxylase (AADC) deficiency (San Sebastian et al. (2014) Mol Ther Methods Clin Dev 3:pii:14049). This new clinically applied technique employs intra-operative MM to visualize parenchymal infusions of AAV2. Its utility is derived from the remarkable correlation between distribution of MRI contrast reagent and eventual transgene expression. However, this close correlation breaks down somewhat with AAV9. Expression of GFP extended into a volume significantly (~3-fold) beyond the volume of the infusion, emphasizing the important role of interstitial or perivascular transport processes engaged as result of the initial pressurized infusion (CED) (Hadaczek et al. (2006) Mol Ther 14:69-78). In the case of AAV2, we would argue that the avidity of the vector for abundant heparan sulphate proteoglycans (Summerford et al. (1998) J Virol 72:1438-1445) helps to restrict AAV2 to the infusion site and matches the distribution of transgene expression closely to the distribution of MRI contrast reagent. In contrast, the primary receptor for AAV9 is not HSPG (Shen et al. (2011) J Biol Chem 286:13532-13540) and this vector may thus engage the perivasculature to achieve a much greater volume of expression for a given infusion volume.

AAV9 evinces a broad tropism in neural tissue (Gray et al. (2011) Mol Ther 19:1058-1069; Hinderer et al. (2014) Molecular Therapy—Methods & Clinical Development 1:14051; Foust et al. (2009) Nat Biotechnol 27:59-65, transducing both neurons and astrocytes as well as perhaps other cell types. The ability of AAV9 to transduce antigen-presenting cells (APC) in the brain has raised concerns with respect to expression of foreign (non-self) proteins (Ciesielska et al. (2013) Mol Ther 21:158-166; Samaranch et al. (2014) Mol Ther 22:329-337; Forsayeth and Bankiewicz (2015) Mol Ther 23:612) in APC and the consequent engagement of neurotoxic adaptive immune responses. This, of course, is not likely to be a problem when self-proteins are expressed, but in the present study we observed, as previously, the activation of Iba1 and upregulation of MHC-II on astrocytes and microglia. Both types of glia are brain APC that have unique individual functions. However, we saw no evidence of microglial transduction by AAV9-GFP even though these cells were clearly responsive to GFP presentation. Our conclusion is that astrocytes are the key APC with respect to adaptive responses to GFP expression.

One of the most striking discoveries about the behavior of AAV serotypes in the brain has been the phenomenon of axonal transport. The ability of neurons to transport intact AAV particles over long distances was first described for AAV2, although this same phenomenon has been described for Herpes simplex (Costantini et al. (1999) *Hum Gene Ther* 10:2481-2494; Diefenbach et al. (2008) *Rev Med Virol* 18:35-51; Lilley et al. (2001) *J Virol* 75:4343-4356; and McGraw and Friedman (2009) *J Virol* 83:4791-4799) and Rabies virus (Gillet et al. (1986) *J Neuropathol Exp Neurol* 45:619-634; Kelly and Strick (2000) *J Neurosci Methods* 103:63-71; Klingen et al. (2008) *J Virol* 82:237-245; Larsen et al. (2007) *Front Neural Circuits* 1:5). In contrast to the primarily retrograde transport of the above viruses, AAV2 undergoes anterograde transport in CNS neurons; that is, particles of AAV2 are transported intact from neuronal cell bodies to synaptic terminals where they are released to be taken up by neurons in distal locations. See, Ciesielska et al. (2011) *Mol Ther* 19:922-927; Kells et al. (2012) *Neurobiol Dis* 48: 228-235; Kells et al. (2009) *Proc Natl Acad Sci USA* 106:2407-2411. This phenomenon requires very efficient distribution and transduction at the primary transduction location and it may explain why it was not discovered earlier since only CED can really achieve this degree of efficiency. Infusion of AAV2 into NHP thalamus results in widespread cortical expression of transgene, primarily pyramidal neurons located in cortical lamina V/VI. Similarly, transduction of NHP putamen or rat striatum with AAV2 results in transgene expression in cell bodies within SNr, which receives projections from striatal GABAergic neurons, but not SNc, which projects to striatum. In contrast to the anterograde transport of AAV2, AAV6 is transported in an exclusively retrograde direction and is almost as neurotropic as AAV2 (Salegio et al. (2013) *Gene Ther.* 20(3):348-52; San Sebastian et al. (2013) *Gene Ther* 20:1178-1183).

Axonal transport of AAV9 was found in this study to be bi-directional. Infusion of AAV9-GFP into putamen led to transgene expression in cortico-striatal neurons that project to putamen and GFP expression was also found in SNc neurons, thereby confirming retrograde transport of this serotype. This phenomenon, significantly more efficient than seen with AAV6 (San Sebastian et al. (2013) *Gene Ther* 20:1178-1183) is valuable in devising therapies for Huntington's disease in which degeneration of both basal ganglionic and cortico-striatal neurons is central to the neuropathology of the disease (Berardelli et al. (1999) *Mov Disord* 14:398-403). Efficient transduction of human putamen with a therapeutic AAV9 enables cortical projections to striatum to be targeted as well.

Additionally, however, the vector was transported in an anterograde direction to SNr and to STN. Labeling of STN neurons was highly dependent on vector dose, more so than in SNr, reflecting the requirement for transport of AAV9-GFP via an indirect route through globus pallidus (GP), by axonal and/or perivascular transport. The ability of AAV9 to spread efficiently beyond the initial putaminal infusion volume suggests a powerful perivascular mechanism. Nevertheless, the phenomenon of bidirectional axonal transport of AAV9 may explain in part why this vector is regarded with such enthusiasm for applications in which very widespread distribution of vector is essential.

Example 5: Delivery of Htt Repressors

Htt repressors (ZFP-TFs, TALE-TFs, CRISPR/Cas-TFs), for example as described in U.S. Patent Publication Nos. 2015/0056705; 2011/0082093; 2013/0253040; and 2015/0335708 and herein are delivered to the striatum of HD model mice, NHP or human subjects using viral (e.g., AAV such as AAV9) as set forth in Example 1.

The Htt repressors exhibit widespread expression and reduce the formation of Htt expression, Htt aggregates; reduce apoptosis; and/or reduce motor deficits (e.g., clasping) in the subjects and are effective in the prevention and/or treatment of HD.

Example 6: Repression of Mutant Htt in HD Patient Fibroblasts and in Neurons Derived from HD Patient Stem Cells ZFP 46025 and 45643 selectively represses mutant HTT in CAG18/45 fibroblasts derived from HD patients (FIG. 8). mRNA encoding the GFP control; ZFP 46025 and ZFP 45643 (0.1, 1, 10 or 100 ng per 50,000 cells) were transfected into HD fibroblasts GM02151 (Coriell Cell Repository) using a Nucleofactor (Lonza). Twenty-four hours after transfection, HTT expression levels were measured by qRT-PCR. Wt Htt (CAG18) and mutant Htt (CAG38) levels in each sample were measured by a custom allele-specific qPCR assay based on SNP rs363099 C/T (exon 29) in triplicates, and normalized to the levels of GAPDH. The Htt/GAPDH ratio for ZFP samples were scaled to that of the mock transfected sample (set to 1). Data are expressed as mean±SD. The data shows selective repression of the mutant Htt allele (CAG45) by both ZFP 46025 and ZFP 45643.

ZFP 46025 and 45643 selectively repress mutant Htt in CAG21/38 fibroblasts derived from HD patients (FIG. 9), mRNA for the GFP control, ZFP 46025 and 45643 (0.1, 1, 10 or 100 ng per 50,000 cells) were transfected into HD fibroblasts ND30259 (Coriell Cell Repository) using a Nucleofactor (Lonza). Twenty-four hours after transfection, Htt expression levels were measured by qRT-PCR. Wt Htt (CAG21) and mutant Htt (CAG38) levels in each sample were measured by a custom allele-specific qPCR assay based on SNP rs362331 C/T (exon 50) in triplicates, and normalized to the levels of GAPDH. The Htt/GAPDH ratio for ZFP samples were scaled to that of the mock transfected sample (set to 1). Data are expressed as mean±SD. The data shows selective repression of the mutant HTT allele (CAG45) by both ZFP 46025 and 45643.

Figure 8:
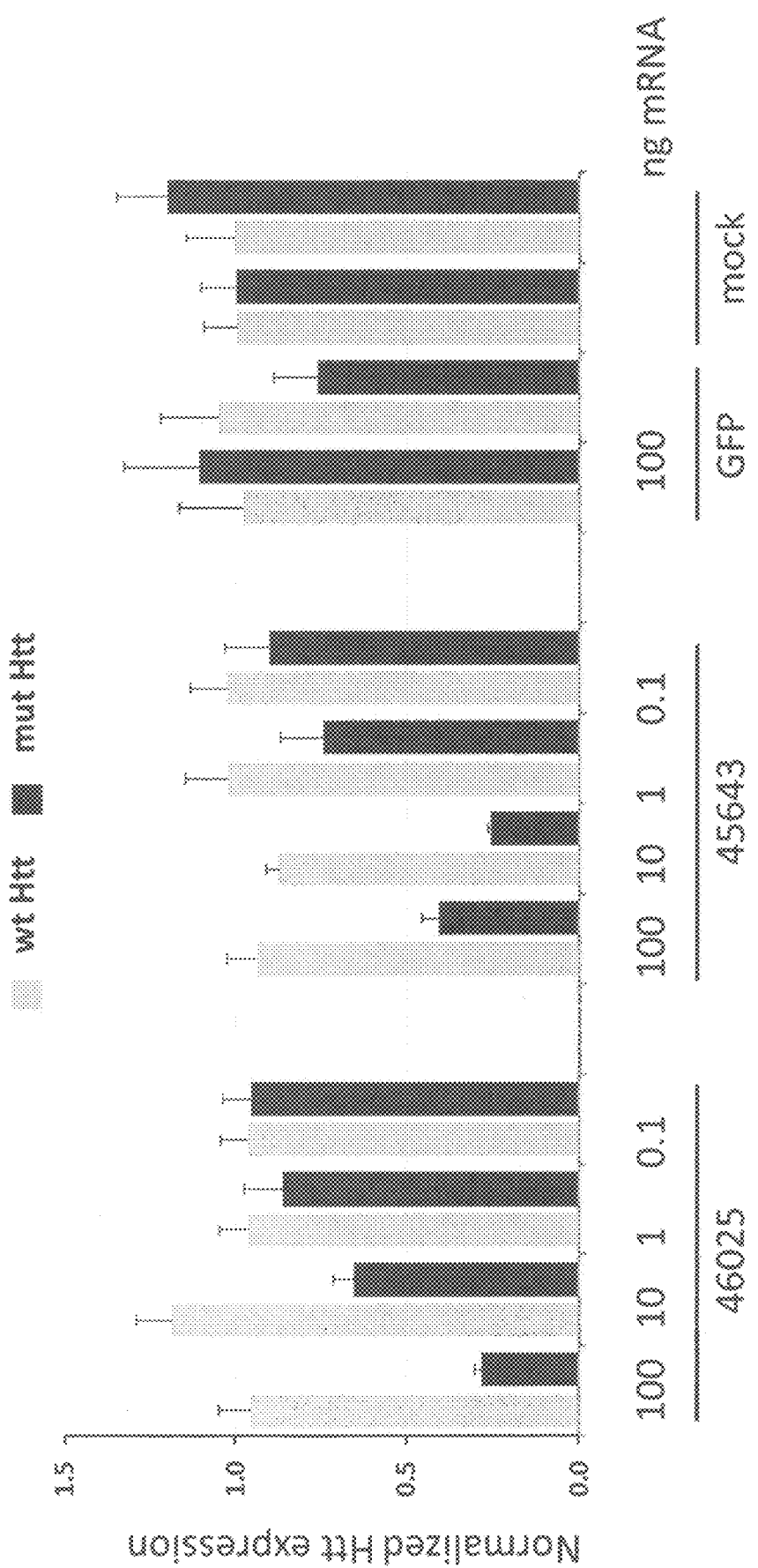
FIG. 8 is a graph showing the expression profiles of either the wild type Htt gene (grey bars, CAG18) or the mutant Htt gene (black bars, CAG45) in fibroblasts from HD patients that have been treated with either ZFP 46025, ZFP 45643 or a GFP control. The data demonstrates that while the expression of the wild type Htt allele is fairly constant in all samples, the cells that had been treated with the mutant Htt-specific ZFPs had decreased expression of the mutant Htt at the higher doses of ZFP mRNA.
Figure 9:
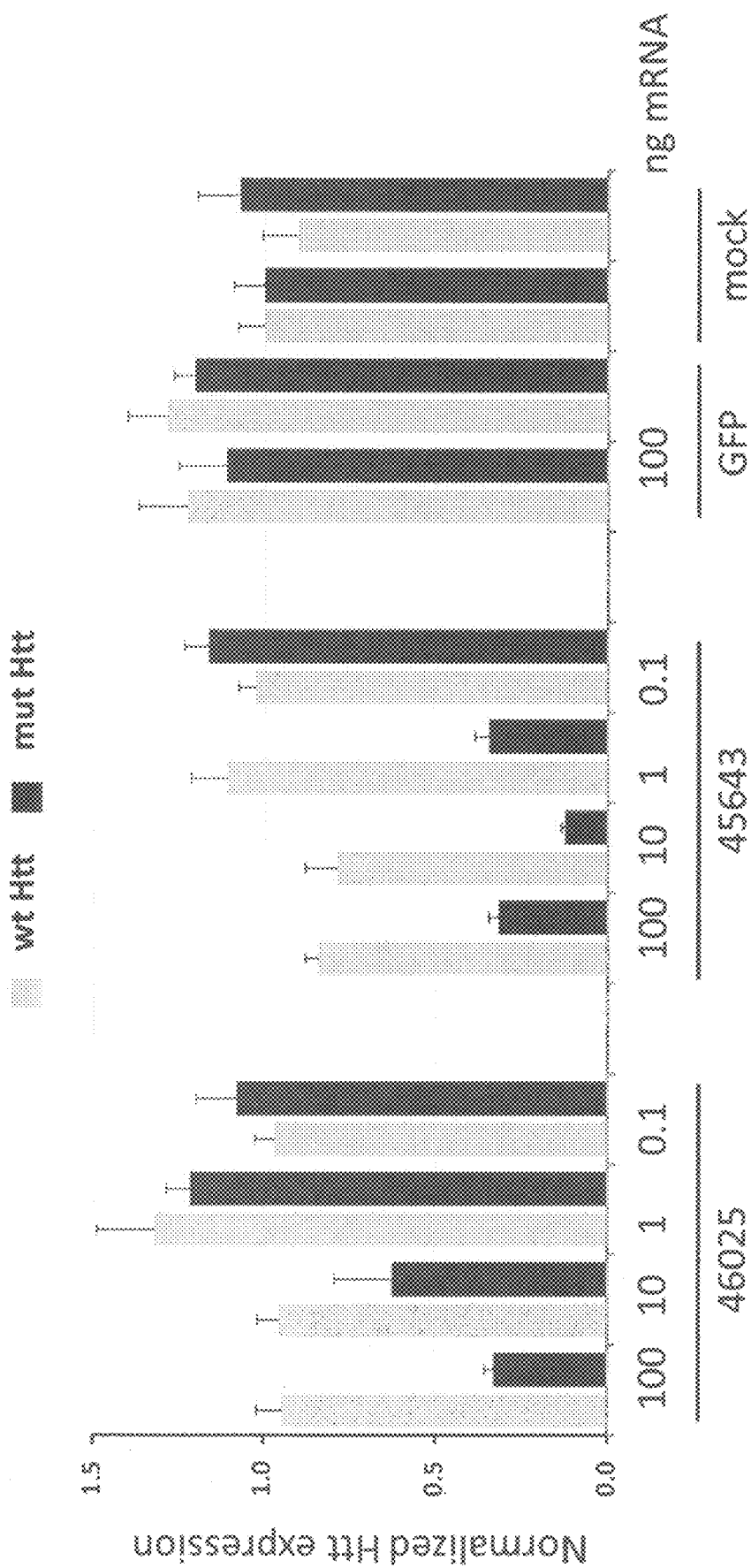
FIG. 9 is a graph showing expression profiles of either the wild type Htt gene (grey bars, CAG21) or the mutant Htt gene (black bars, CAG38) in fibroblasts from HD patients that have been treated with either ZFP 46025, ZFP 45643 or a GFP control. The data demonstrates that while the expression of the wild type Htt allele is fairly constant in all samples, the cells that had been treated with the mutant Htt-specific ZFPs had decreased expression of the mutant Htt at the higher doses of ZFP mRNA.

Data in FIGS. 8 and 9 show that ZFP 46025 and 45643 can selectively repress transcription from mutant Htt alleles in patient-derived cells that contain different CAG repeat lengths on both wild type and mutant Htt alleles.

Figure 10:
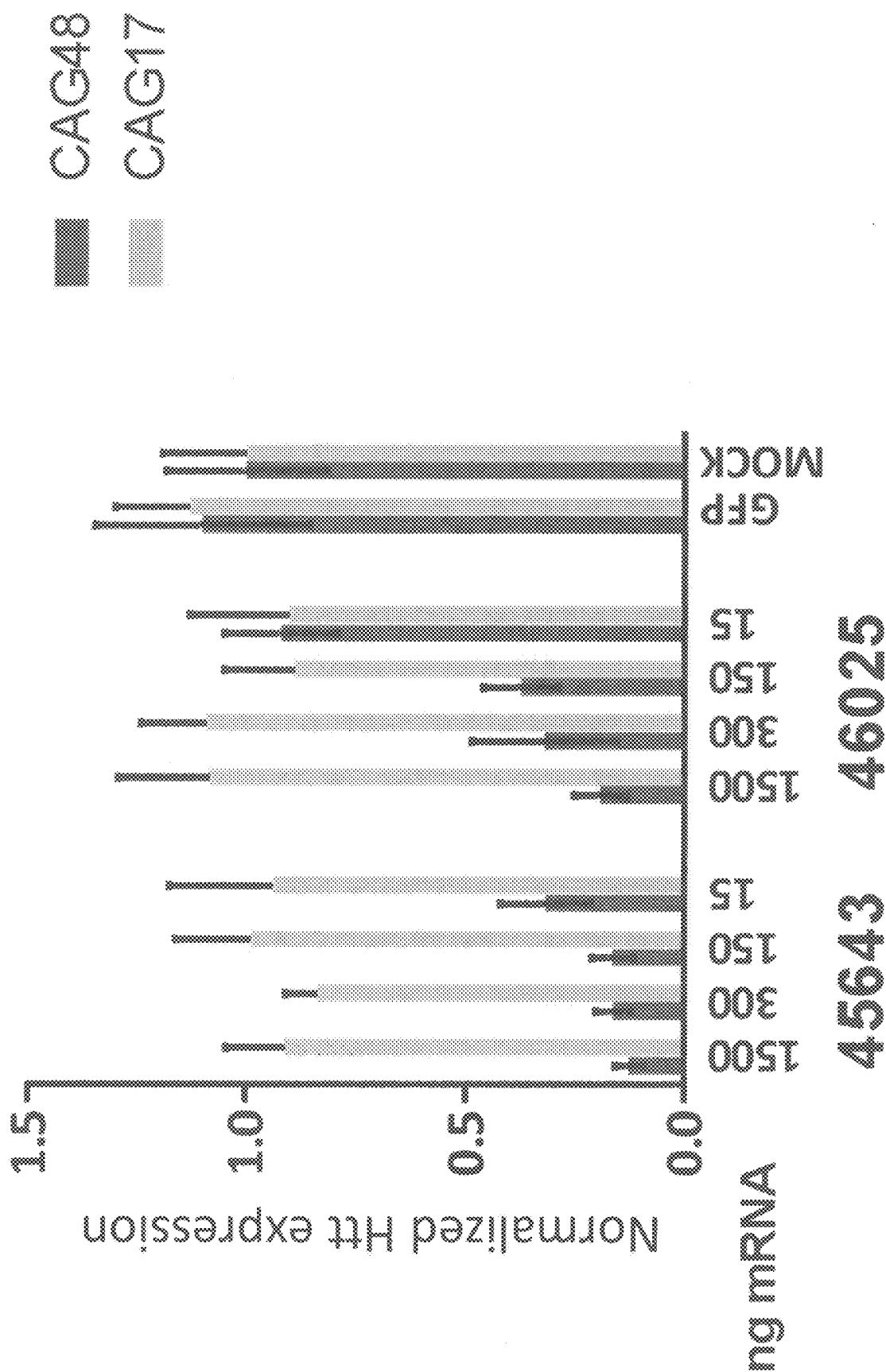
FIG. 10 is a graph showing expression profiles of either the wild type Htt gene (grey bars, CAG17) or the mutant Htt gene (black bars, CAG48) in neurons that have been differentiated from HD embryonic stem cells. The data demonstrates that at the higher doses of mRNA encoding the ZFPs, the mutant Htt gene was repressed while the wild type Htt allele was not.

ZFP 46025 and 45643 selectively repress mutant Htt in CAG17/48 neurons by transient mRNA transfection (FIG. 10). mRNA for the GFP control, ZFP 46025 and 45643 (15, 150, 300 or 1,500 ng per 150,000 cells) were transfected into neurons differentiated from HD embryonic stem cells (ESC) GENEA020 (GENEA/CHDI) using a Nucleofactor (Lonza). Two days after transfection, Htt expression levels were measured by qRT-PCR. Wild type Htt (CAG17) and mutant Htt (CAG48) levels in each sample were measured by an allele-specific qPCR assay based on SNP rs362307 in exon 67 (Applied Biosystems) in triplicates, and normalized to the levels of GAPDH. The Htt/GAPDH ratio for ZFP samples were scaled to that of the mock transfected sample (set to 1). Data are expressed as mean±SD. The data shows selective repression of the mutant Htt allele (CAG48) by both ZFP 46025 and 45643 in HD neurons.

Figure 11A:
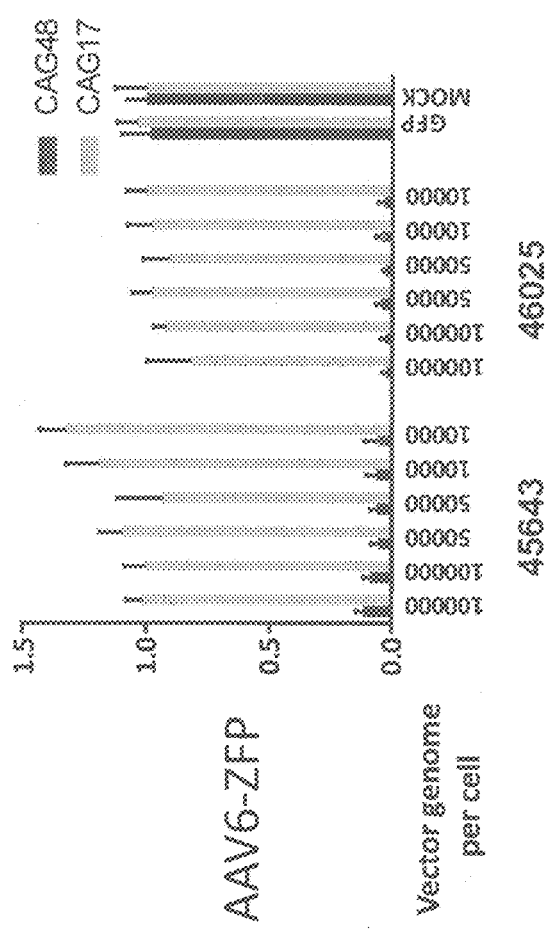
FIGS. 11A and 11B are graphs showing Htt repression in CAG17/48 differentiated neurons where the ZFPs using were delivered using either AAV6 or AAV9 viral vectors. AAV6 vectors (FIG. 11A) or AAV9 vectors (FIG. 11B) encoding ZFP 46025, 45643 or GFP control were used to infect neurons differentiated from HD embryonic stem cells (ESC) GENEA020 (GENEA/CHDI) in duplicate. The data demonstrates that the mutant Htt allele was repressed by the ZFPs when delivered either by AAV6 or AAV9 as compared to cells treated with the GFP control or those that had been put through a mock infection protocol.

The experiments were also carried out on the differentiated CAG17/48 neurons where the ZFPs using were delivered using either AAV6 or AAV9 viral vectors. AAV6 vectors encoding ZFP 46025, 45643 or GFP control were used to infect neurons differentiated from HD embryonic stem cells (ESC) GENEA020 (GENEA/CHDI) in duplicate. AAV doses used were 1E+4, 5E+4, or 1E+5 vector genome (vg) per cell for ZFPs and 1E+5 vg per cell for GFP. Twenty-one days after infection, HTT expression levels were measured by qRT-PCR. Wt Htt (CAG17) and mutant Htt (CAG48) levels in each sample were measured by an allele-specific qPCR assay based on SNP rs362307 in exon 67 (Applied Biosystems) in triplicates, and normalized to the levels of GAPDH. The Htt/GAPDH ratio for ZFP samples were scaled to that of the mock transfected sample (set to 1). Data are expressed as mean±SD (FIG. 11A).

Figure 11B:
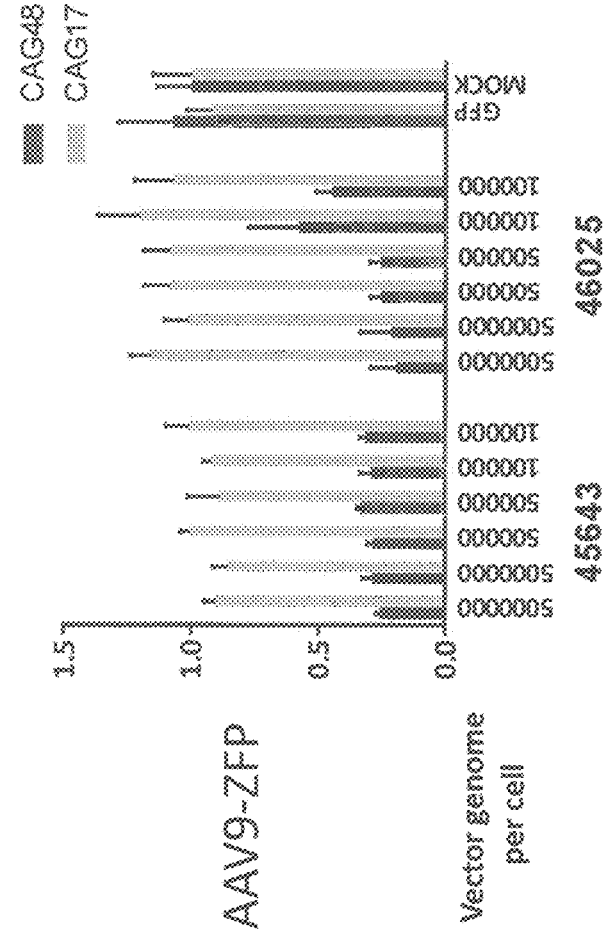

AAV9 vectors encoding ZFP 46025, 45643 or GFP control were used to infect neurons differentiated from HD embryonic stem cells (ESC) GENEA020 (GENEA/CHDI) in duplicate. AAV doses used were 1E+5, 5E+5 or 5E+6 vector genome (vg) per cell for ZFPs and 5E+6 vg per cell for GFP. Twenty-one days after infection, HTT expression levels were measured by qRT-PCR. Wild type Htt (CAG17) and mutant Htt (CAG48) levels in each sample were measured by an allele-specific qPCR assay based on SNP rs362307 in exon 67 (Applied Biosystems) in triplicates, and normalized to the levels of GAPDH. The Htt/GAPDH ratio for ZFP samples were scaled to that of the mock transfected sample (set to 1). Data are expressed as mean±SD (FIG. 11B).

Figure 12B:
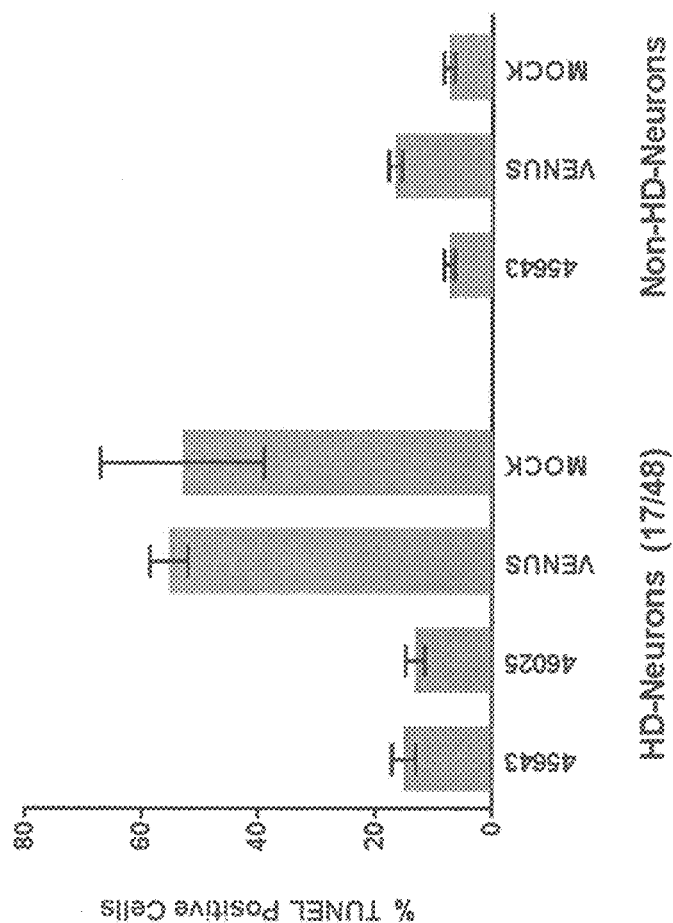
FIGS. 12A and 12B are graphs depicting the effect of treatment with the ZFPs on phenotypic characteristics of the HD neurons.
Figure 12A:
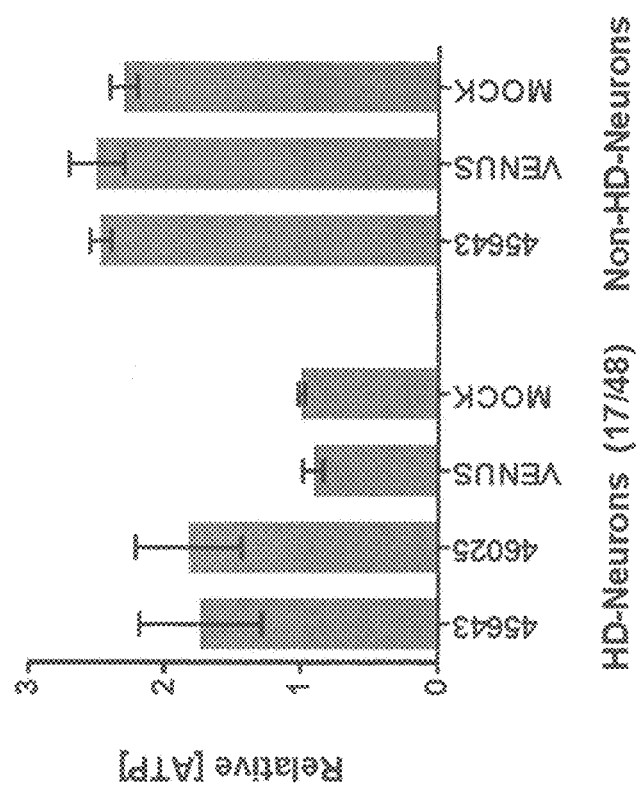

Example 7: ZFP 46025 and 45643 Rescue Cellular Phenotypes that are Related to HD Previous studies have shown phenotypic changes associated with expanded CAG repeats in HD patient-derived cells (Jung-il et al. (2012) *Biochemical Journal* 446(3):359-371; HD IPSC Consortium (2012) *Cell Stem Cell* 11(2):264-278; An et al. (2012) *Cell Stem Cell* 11(2):253-263). In agreement with these published findings, we found that CAG17/48 neurons had a significant decrease in intracellular ATP levels compared to non-HD (normal) neurons (FIG. 12A). Twenty-one days after neurons were infected with lentiviral vectors encoding ZFP 46025 or ZFP 45643, intracellular ATP levels increased 1.7- and 1.8-fold compared to control cells, respectively, indicating that mutant Htt silencing rescues the energetic defect in HD neurons. Another phenotype of HD neurons in vitro is the increased susceptibility to programmed cell death. With growth factor withdrawal, the percentage of CAG17/48 neurons undergoing apoptosis was 4-5-fold higher than that of normal neurons (FIG. 12B). At 12 days after lentiviral infection, followed by two days of growth factor withdraw, ZFP 46025 and 45643 reduced the number of apoptotic cells to that seen in wild-type cells.

Intracellular ATP levels of cultured neurons, derived from an HD patient (CAG17/48) or a normal subject, were measured using the CellTiter-Glo® Luminescent Assay (Promega), where cell numbers in each sample were determined using the ApoLive-Glo® assay (Promega). Neurons were infected in triplicate with LV expressing either YFP-Venus or ZFP-TF (45643 or 46025-KOX-2A-Venus) at an MOI of 500.

At 21 days after lentiviral infection, intracellular [ATP] levels in neurons were measured using the CellTiter-Glo Luminescent Assay (Promega) according to manufacturer's instructions. Luminescence values were normalized to the cell number in each sample. ATP level per cell values from different cells/treatment were then normalized to that of mock-infected HD neurons (set as 1). Data (FIG. 12A) are expressed as mean±SD.

Cell death of HD and non-HD neurons induced by growth factor withdrawal was measured using a terminal deoxynucleotidyl transferase dUTP nick end labeling (TUNEL) assay. Neurons were infected in triplicate with LV expressing either YFP-Venus or ZFP-TF (45643 or 46025-KOX-2A-Venus) at an MOI of 500. The cells were cultured for 12 days then media was changed to fresh neurobasal media without any additive (growth factors). Cells were kept in this growth factor withdrawal media for 48 hours. TUNEL assay was performed using the ApoBrdU Red DNA fragmentation kit (BioVision). Neurons were fixed with 4% paraformaldehyde on ice for 15 min. Apoptosis was assessed by quantifying TUNEL-positive cells according to the manufacturer recommendations (ApoBrdU Red DNA fragmentation kit, BioVision). Flow cytometry was used to measure apoptosis by anti-BrdU-Red staining. Data (FIG. 12B) are expressed as mean±SD.

Thus, repressors as described herein provide therapeutic benefits by rescuing HD-related phenotypes, including, but not limited to, decreasing cell death, increasing cell function (as measured by intracellular ATP levels) and decreasing cell susceptibility to apoptosis as compared to untreated cells.

Example 8: ZFP 46025 and ZFP 45643 Repress Mutant Htt in Mouse Striatum

Figure 13B:
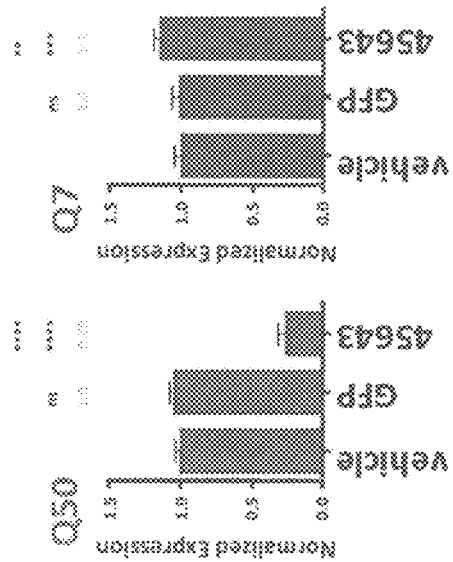
FIGS. 13A through 13C are graphs depicting the in vivo activity of ZFPs were tested in HdhQ50/Hdh+ (Q50) heterozygous mice by intrastriatal injection of AAV9 vectors encoding ZFP 46025, ZFP 45643 or GFP control. The Q50 mice contain a knock-in allele where exon 1 of the endogenous mouse Hdh gene was replaced with exon 1 of the human Htt gene with 48 CAGs. At 5 weeks after injection, allele-specific qRT-PCR analysis of treated striatum showed that ZFP 45643 and ZFP 46025 repressed the mutant Htt allele (Q50) by 79% and 74%, respectively, relative to vehicle injected control; the wild type allele (Q7) was not regulated by either ZFP (FIGS. 13A and 13B). Activity of ZFP 45643 was also tested at 12 weeks after injection (FIG. 13C), and significant repression (70%) of mutant Htt (Q50) was observed with no repression of the wild type allele (Q7).
Figure 13A:
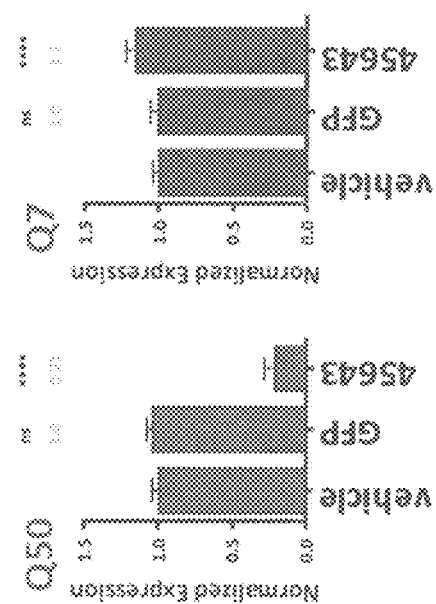
Figure 13C:
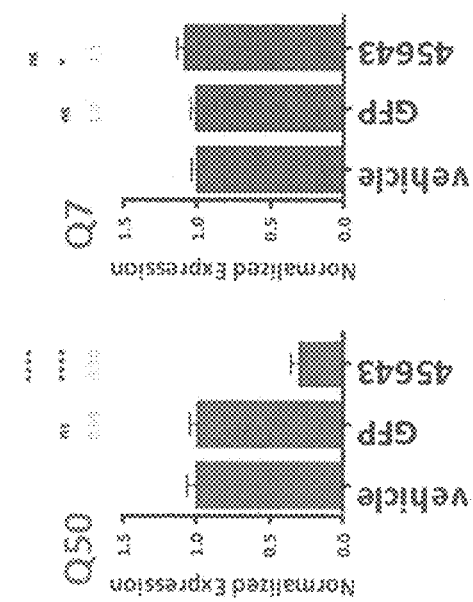

In vivo activity of ZFPs were tested in HdhQ50/Hdh+ (Q50) heterozygous mice (White et al. (1997) *Nature Genetics* 17:404-410) by intrastriatal injection of AAV9 vectors encoding ZFP 46025, ZFP 45643 or GFP control. The Q50 mice contain a knock-in allele where exon 1 of the endogenous mouse Hdh gene was replaced with exon 1 of the human Htt gene with 48 CAGs. At 5 weeks after injection, allele-specific qRT-PCR analysis of treated striatum showed that ZFP 45643 and ZFP 46025 repressed the mutant Htt allele (Q50) by 79% and 74%, respectively, relative to vehicle injected control; the wild type allele (Q7) was not regulated by either ZFP (FIGS. 13A and 13B). Activity of ZFP 45643 was also tested at 12 weeks after injection (FIG. 13C), and significant repression (70%) of mutant Htt (Q50) was observed with no repression of the wild type allele (Q7). No overt toxicity was observed in any of the animals over the course of the study. Behavioral studies (e.g., clasping studies) are also performed and show that the repressors as described herein provide a therapeutic (clinical) benefit in vivo.

HdhQ50/Hdh+(Q50) heterozygous mice (mixed gender) received bilateral intrastriatal injection of AAV9 vectors (ZFP 46025, 45643 or GFP, n=4 per group) or formulation buffer (vehicle, n=3) at 10-11 weeks of age. Two 3-µl injections were placed into each striatum (for a total of 6 µl and 1.1E+10 vector genome per striatum). The coordinates used for the anterior infusion was A/P +1.4, M/L +/−1.7, D/V −3.5 and for the posterior infusion was A/P +0.2, M/L +/−2.3, D/V −3.2. At five weeks (ZFP 46025 and 45643) and 12 weeks (ZFP 45643) after injection, mice were sacrificed and each striatum was dissected into three (anterior, middle and posterior) slices for RNA isolation and qRT-PCR analysis. Expression from the mutant Htt allele (Q50) and the wt allele (Q7) were measured by allele-specific qPCR assays, Htt levels were normalized to the geometric mean of ATP5B, RPL38 and EIF4A2 levels. (ns: $p>0.05$, *: $p<0.05$, : $p<0.01$, *: $p<0.001$, ****: $p<0.0001$, one way ANOVA with Sidak test).

As shown in FIG. 13, allele-specific qRT-PCR analysis of treated striatum showed that ZFP 45643 and ZFP 46025 repressed the mutant Htt allele (Q50) by 79% and 74%, respectively, relative to vehicle injected control; the wild type allele (Q7) was not regulated by either ZFP. Activity of ZFP 45643 was also tested at 12 weeks after injection and significant repression (70%) of mutant Htt (Q50) was observed with no repression of the wild type allele (Q7).

Thus, Htt repressors as described herein exhibit widespread expression and reduce the formation of Htt expression, Htt aggregates; reduce apoptosis; and/or reduce motor deficits (e.g., clasping) in subjects and are effective in the prevention and/or treatment of HD.

Example 9: Measuring Therapeutic Efficacy of ZFP 46025 and ZFP 45643

HD patients are treated with ZFP 46025 or ZFP 45643 at varying doses. HD patients are evaluated using the UHDRS scale and show improvement following treatment. Efficacy is also measured by PET imaging analysis using $^{18}$FMNI-659, a PET tracer for PDE10A, and MRI. In brief, regions of the brain (e.g. areas within putamen) that are exposed to ZFP (e.g. AAV9 vector encoding the ZFP) are identified by Gadolinium contrast agent that is mixed with the ZFP formulation and MiI; before and after treatment, patients are given approximately 5 mCi of $^{18}$FMNI-659 at a mass dose of about 5 μg over a three minute infusion period. Serial 3D PET images are acquired for a period of 90 minutes using a PET scanner. MM images are also obtained using a MiI scanner, and the PET images are aligned with the MiI images to generate anatomy-based visuals for analysis. Standard uptake values are calculated for the basal ganglia nuclei (which includes the globus pallidus, caudate, and putamen (striatum)) and normalized to a reference region such as the cerebellum (Russell et al., ibid). PDE10A PET signals in brain regions that are exposed to the ZFP, identified by MM at time of treatment, are measured after treatment and compared to signal levels in the same region before treatment. Treatment of the HD patients with ZFP46025 or ZFP45643 protects the patients from any additional loss of medium spiny neuron (measured by PDE10A levels) and from the further development of overt clinical symptoms. In some patients, treatment with the ZFPs reverses the symptoms of HD.

All patents, patent applications and publications mentioned herein are hereby incorporated by reference for all purposes in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A cell comprising a non-naturally occurring zinc finger protein transcription factor (ZFP-TF) that represses expression of mutant human or mouse Huntingtin (Htt) gene (mHtt), the zinc finger protein transcription factor comprising:
   (a) a transcriptional repression domain; and
   (b) a zinc finger protein designated SBS #45643 or SBS #46025, the zinc finger protein comprising 5 zinc finger domains ordered F1 to F5 as follows:

(i)
   F1:
   QSGDLTR;    (SEQ ID NO: 1)

F2:
   QSGDLTR;    (SEQ ID NO: 1)

F3:
   QSGDLTR;    (SEQ ID NO: 1)

F4:
   KHGNLSE;    (SEQ ID NO: 2)
   and

F5:
   KRCNLRC;    (SEQ ID NO: 3)
   or (ii)
   F1:
   CPSHLTR;    (SEQ ID NO: 4)

F2:
   QSGDLTR;    (SEQ ID NO: 1)

F3:
   KHGNLSE;    (SEQ ID NO: 2)

F4:
   KRCNLRC;    (SEQ ID NO: 3)
   and

F5:
   RQFNRHQ.    (SEQ ID NO: 5)

2. The cell of claim 1, comprising a polynucleotide encoding one or more zinc finger protein-transcription factors.

3. The cell of claim 2, wherein the polynucleotide is carried by an AAV vector.

4. The cell of claim 1, wherein the cell is a fibroblast or a neuron.

5. A method of rescuing a cellular phenotype in an HD neuron comprising a mutant Htt gene having at least 35 expanded CAG repeats, the method comprising bilaterally injecting into the striatum of a mouse or human an adeno-associated virus (AAV) vector comprising a sequence encoding a non-naturally occurring zinc finger protein transcription factor (ZFP-TF) that represses expression of mutant human or mouse Htt gene (mHtt) in the HD neuron, the zinc finger protein transcription factor comprising:

(a) a transcriptional repression domain comprising a Krüppel associated box (KRAB) domain; and (b) a zinc finger protein designated SBS #45643 or SBS #46025, the zinc finger protein comprising 5 zinc finger domains ordered F1 to F5 as follows:

(i)
F1:
QSGDLTR; (SEQ ID NO: 1)

F2:
QSGDLTR; (SEQ ID NO: 1)

F3:
QSGDLTR; (SEQ ID NO: 1)

F4:
KHGNLSE; (SEQ ID NO: 2)
and

F5:
KRCNLRC; (SEQ ID NO: 3)
or (ii)
F1:
CPSHLTR; (SEQ ID NO: 4)

F2:
QSGDLTR; (SEQ ID NO: 1)

F3:
KHGNLSE; (SEQ ID NO: 2)

F4:
KRCNLRC; (SEQ ID NO: 3)
and

F5:
RQFNRHQ. (SEQ ID NO: 5)

6. The method of claim 5, wherein the rescued cellular phenotype is selected from the group consisting of decreasing cell death, increasing cell function and decreasing cell susceptibility to apoptosis.

7. The method of claim 6, wherein ATP levels in the HD neuron are increased.

8. The method of claim 7, wherein susceptibility to apoptosis in the HD neuron is reduced.

9. The method of claim 5, wherein Huntington's disease is treated and/or prevented in the mouse or human following bilateral injection of said AAV vector.

* * * * *